United States Patent
Wang et al.

(10) Patent No.: US 12,291,515 B2
(45) Date of Patent: May 6, 2025

(54) PYRROLIDINE DERIVATIVE AND USE THEREOF

(71) Applicants: Zheming Wang, Hangzhou (CN); Rushi Biotech (Hangzhou) Co., Ltd, Hangzhou (CN)

(72) Inventors: Zheming Wang, Hangzhou (CN); Hao Tan, Hangzhou (CN)

(73) Assignees: Zheming Wang, Hangzhou (CN); Rushi Biotech (Hangzhou) Co., Ltd, Hangzhou (CN)

( * ) Notice: Subject to any disclaimer, the term of this patent is extended or adjusted under 35 U.S.C. 154(b) by 0 days.

(21) Appl. No.: 18/080,732

(22) Filed: Dec. 13, 2022

(65) Prior Publication Data
US 2023/0192651 A1    Jun. 22, 2023

(30) Foreign Application Priority Data
Dec. 22, 2021    (CN) .......................... 202111595168.8

(51) Int. Cl.
| | | |
|---|---|---|
| *C07D 401/12* | (2006.01) | |
| *C07D 401/14* | (2006.01) | |
| *C07D 405/14* | (2006.01) | |
| *C07D 409/14* | (2006.01) | |

(52) U.S. Cl.
CPC ......... *C07D 401/12* (2013.01); *C07D 401/14* (2013.01); *C07D 405/14* (2013.01); *C07D 409/14* (2013.01)

(58) Field of Classification Search
CPC .. C07D 401/12; C07D 401/14; C07D 405/14; C07D 409/14
See application file for complete search history.

(56) References Cited

FOREIGN PATENT DOCUMENTS

EP      3279192 A1 *  2/2018  .............. A61P 35/00

OTHER PUBLICATIONS

Vieira, Rodrigo De Oliveira, et al. "Use of piperidine and pyrrolidine in Knoevenagel condensation." Organic & Medicinal Chemistry International Journal 5 vol. 4 pp. 113-116. (Year: 2018).*
Wilsbacher et al., Molecular Cancer Therapeutics 2017, vol. 16(7), pp. 1236-1245. (Year: 2017).*

* cited by examiner

*Primary Examiner* — Craig D Ricci
*Assistant Examiner* — Janet L Coppins

(57) ABSTRACT

The present invention discloses a pyrrolidine derivative or its optically active isomer, or a pharmaceutically acceptable salt thereof, which is useful as an NAMPT inhibitor, and useful as a potential agent for the chemotherapy of a variety of diseases associated with abnormal $NAD^+$ expression. The pyrrolidine derivative has pyrrolidine as a parent structure, to which pyridinylurea (or substituted pyridinylurea) is attached by an intermediate aliphatic chain, and a side arylformyl (or heterocyclylformyl) group is attached. This structure is an optimized structure of the NAMPT inhibitor FK866, in which the acrylamido group is replaced by a urea structure, to increases the water solubility of the compound. Moreover, the difficulty in synthesis is reduced accordingly, which is conducive to the subsequent industrial production.

1 Claim, No Drawings

PYRROLIDINE DERIVATIVE AND USE THEREOF

CROSS-REFERENCE TO RELATED APPLICATION

The present application claims priority from Chinese Patent Application No. 202111595168.8 filed on Dec. 22, 2021, the contents of which are incorporated herein by reference in their entirety.

TECHNICAL FIELD

The present invention relates to a pyrrolidine compound, and particularly to a pyrrolidine derivative and use thereof.

BACKGROUND $NAD^+$ is a key coenzyme for cellular redox and a key substrate for $NAD^+$ dependent enzymes, which is involved in a wide range of physiological processes, for example, redox, DNA repair, gene expression, RNA processing, immune system, inflammation and living clock regulation in organisms. Abnormal $NAD^+$ level incurs a range of metabolic diseases and aging, and normal $NAD^+$ level in the body is maintained by a salvage pathway, where NAMPT is a key rate-limiting enzyme in one of two salvage pathways.

Tumor cells have high glucose uptake capacity and high glycolysis rate. Such abnormal metabolic changes require a large amount of redox coenzyme $NAD^+$. NAMPT is essential for the supplementation of intracellular $NAD^+$, and the development of many cancers is associated with the increased expression of NAMPT.

Through the study of NAMPT, it is found that reduced expression of NAMPT is closely related to the dysregulation of cancer signaling pathways and that tumor cells are more susceptible to NAMPT inhibition than normal cells. Therefore, NAMPT can be used as a new target for cancer therapy. More and more evidences show that NAMPT inhibitors have potential as anticancer drugs. Small molecule inhibitors of NMAPT can inhibit the intracellular $NAD^+$ salvage pathway, to reduce the $NAD^+$ level and eventually induce the tumor cell death.

SUMMARY

To solve the disadvantages in the prior art, an object of the present invention is to provide a pyrrolidine derivative and use thereof.

The following technical solutions are adopted in the present invention.

The present invention provides a pyrrolidine derivative of Formula (I), or its optically active isomer of Formula (II), or its optically active isomer of Formula (III), or a pharmaceutically acceptable salt thereof:

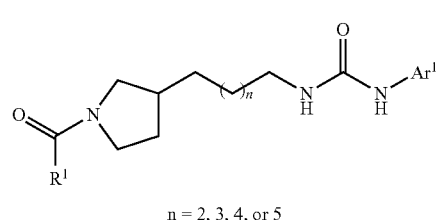

Formula (I)

n = 2, 3, 4, or 5

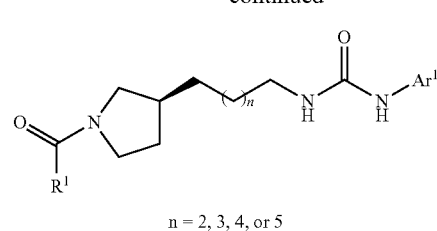

Formula (II)

n = 2, 3, 4, or 5

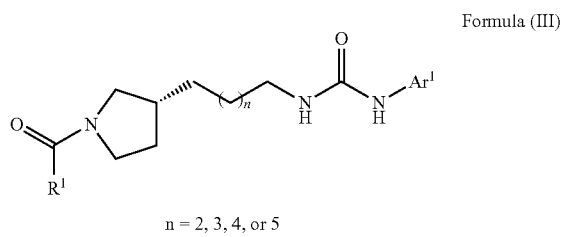

Formula (III)

n = 2, 3, 4, or 5 where $R^1$ is a heteroatom containing cyclic alkyl or an aromatic ring system, including a five-membered heterocycloalkyl group, a six-membered heterocycloalkyl group, phenyl, heteroaryl, or benzoheterocylcyl, which is optionally mono-, di-, or trisubstituted, with a substituent including $C_1$-$C_3$ alkyl, $C_1$-$C_3$ alkoxy or hydroxyl; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (IV) or a pharmaceutically acceptable salt thereof:

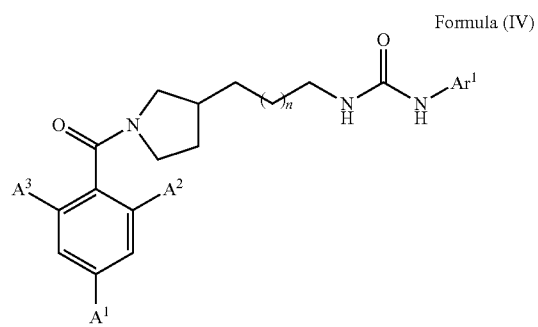

Formula (IV)

n = 2, 3, 4, or 5 where $A^1$ is hydrogen, hydroxyl, $C_1$-$C_3$ alkyl or $C_1$-$C_3$ alkoxy;

$A^2$ is hydrogen, hydroxyl, $C_1$-$C_3$ alkyl or $C_1$-$C_3$ alkoxy;

$A^3$ is hydrogen, hydroxyl, $C_1$-$C_3$ alkyl or $C_1$-$C_3$ alkoxy; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (V) or a pharmaceutically acceptable salt thereof:

Formula (V)

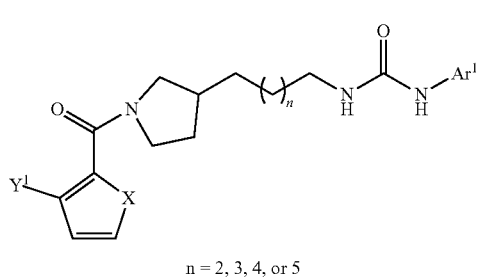

n = 2, 3, 4, or 5 where X is a heteroatom, including nitrogen, oxygen, or sulfur;

$Y^1$ is hydrogen, fluoro, chloro, bromo, iodo or hydroxyl; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (VI) or a pharmaceutically acceptable salt thereof:

Formula (VI)

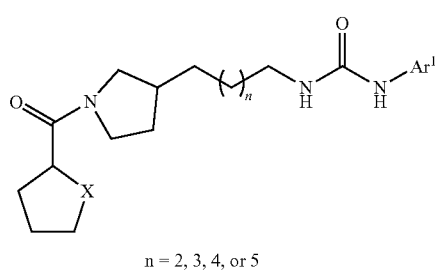

n = 2, 3, 4, or 5 where X is a heteroatom, including nitrogen, oxygen, or sulfur; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (VII) or a pharmaceutically acceptable salt thereof:

Formula (VII)

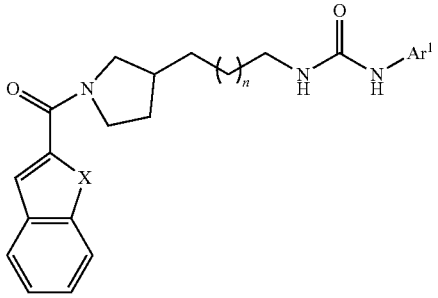

n = 2, 3, 4, or 5 where X is a heteroatom, including nitrogen, oxygen, or sulfur; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (VIII) or Formula (IX), or a pharmaceutically acceptable salt thereof:

Formula (VIII)

Formula (IX)

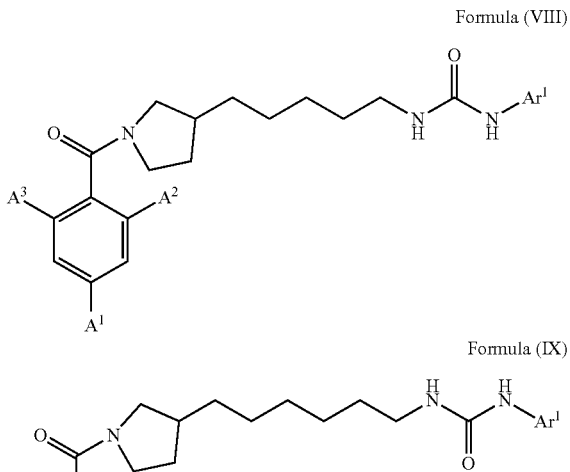

where $A^1$ is hydrogen, hydroxyl, $C_1$-$C_3$ alkyl or $C_1$-$C_3$ alkoxy;

$A^2$ is hydrogen, hydroxyl, $C_1$-$C_3$ alkyl or $C_1$-$C_3$ alkoxy;

$A^3$ is hydrogen, hydroxyl, $C_1$-$C_3$ alkyl or $C_1$-$C_3$ alkoxy; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (X) or Formula (XI), or a pharmaceutically acceptable salt thereof:

Formula (X)

Formula (XI)

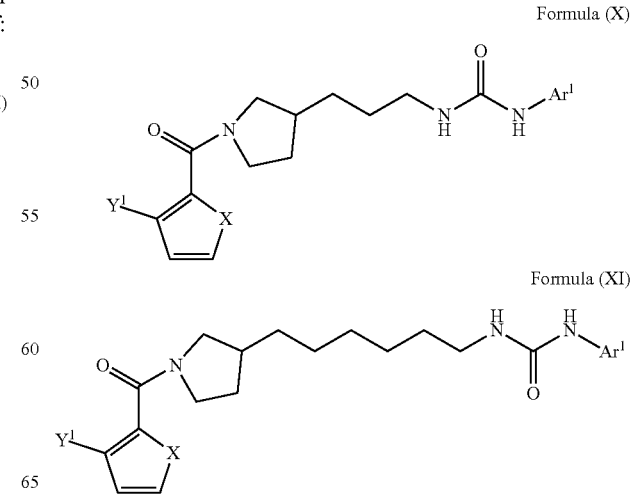

where X is a heteroatom, including nitrogen, oxygen, or sulfur; and $Y^1$ is hydrogen, fluoro, chloro, bromo, iodo or hydroxyl; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (XII) or Formula (XIII), or a pharmaceutically acceptable salt thereof:

Formula (XII)

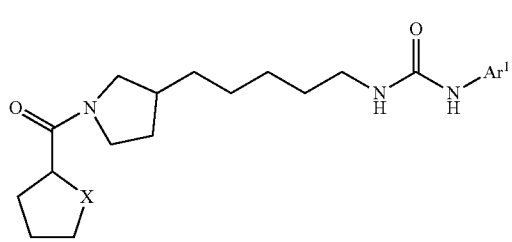

Formula (XIII)

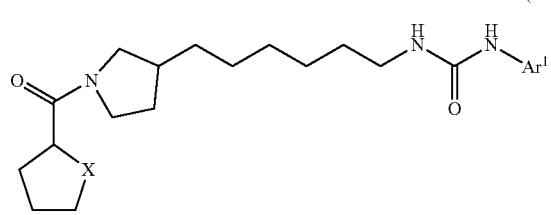

where X is a heteroatom, including nitrogen, oxygen, or sulfur; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (XIV) or Formula (XV), or a pharmaceutically acceptable salt thereof:

Formula (XIV)

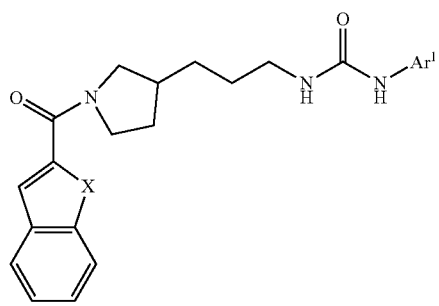

-continued

Formula (XV)

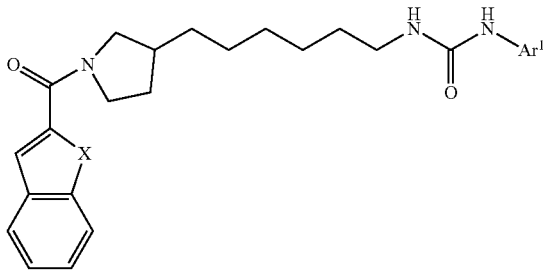

where X is a heteroatom, including nitrogen, oxygen, or sulfur; and $Ar^1$ is an aromatic ring system, including phenyl or heteroaryl, which is optionally mono-, di-, or trisubstituted, with a substituent including halo or hydroxyl.

The present invention provides a pyrrolidine derivative of Formula (XVI), Formula (XVII), Formula (XVIII) or Formula (XIX), or a pharmaceutically acceptable salt thereof:

Formula (XVI)

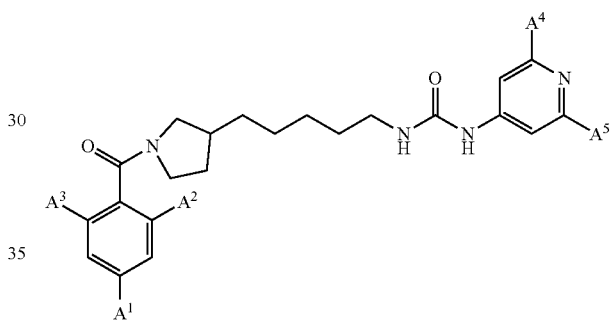

Formula (XVII)

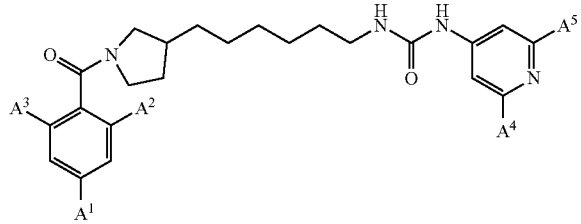

Formula (XVIII)

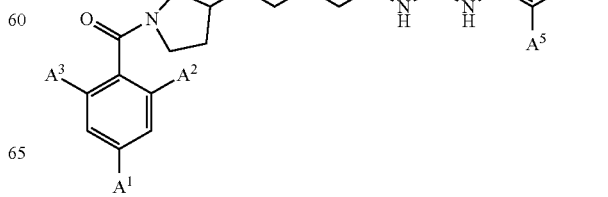

-continued

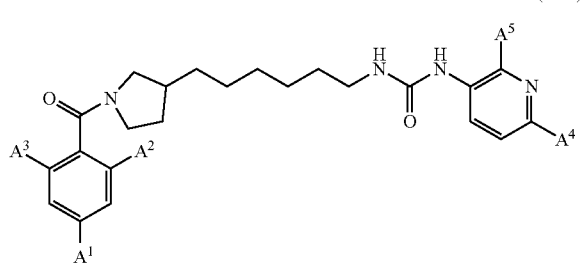

Formula (XIX)

$A^1$ is hydrogen, hydroxyl, $C_1$-$C_3$ alkyl or $C_1$-$C_3$ alkoxy;
$A^2$ is hydrogen, hydroxyl, $C_1$-$C_3$ alkyl or $C_1$-$C_3$ alkoxy;
$A^3$ is hydrogen, hydroxyl, $C_1$-$C_3$ alkyl or $C_1$-$C_3$ alkoxy;
$A^4$ is hydrogen, fluoro, chloro, bromo, iodo or hydroxyl; and
$A^5$ is hydrogen, fluoro, chloro, bromo, iodo or hydroxyl.

The present invention provides a pyrrolidine derivative of Formula (XX), Formula (XXI), Formula (XXII) or Formula (XXIII), or a pharmaceutically acceptable salt thereof:

Formula (XX)

Formula (XXI)

Formula (XXII)

Formula (XXIII)

where X is a heteroatom, including nitrogen, oxygen, or sulfur;
$Y^1$ is hydrogen, fluoro, chloro, bromo, iodo or hydroxyl;
$A^4$ is hydrogen, fluoro, chloro, bromo, iodo or hydroxyl; and
$A^5$ is hydrogen, fluoro, chloro, bromo, iodo or hydroxyl.

The present invention provides a pyrrolidine derivative of Formula (XXIV), Formula (XXV), Formula (XXVI) or Formula (XXVII), or a pharmaceutically acceptable salt thereof:

Formula (XXIV)

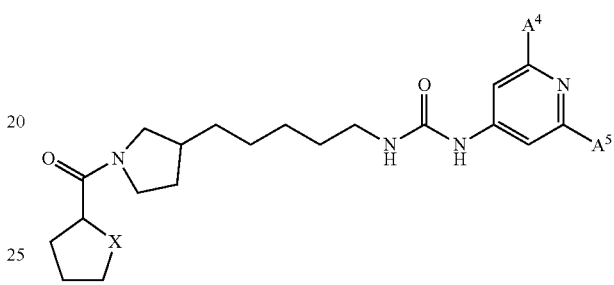

Formula (XXV)

Formula (XXVI)

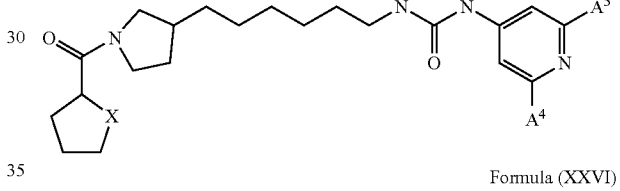

Formula (XXVII)

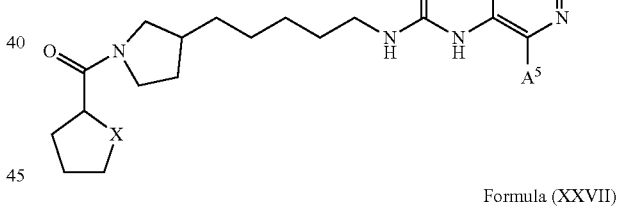

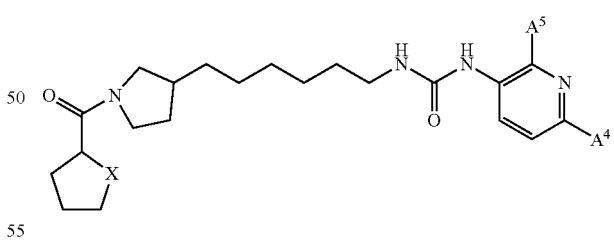

where X is a heteroatom, including nitrogen, oxygen, or sulfur;
$A^4$ is hydrogen, fluoro, chloro, bromo, iodo or hydroxyl; and
$A^5$ is hydrogen, fluoro, chloro, bromo, iodo or hydroxyl.

The present invention provides a pyrrolidine derivative of Formula (XXVIII), Formula (XXIX), Formula (XXX) or Formula (XXXI), or a pharmaceutically acceptable salt thereof:

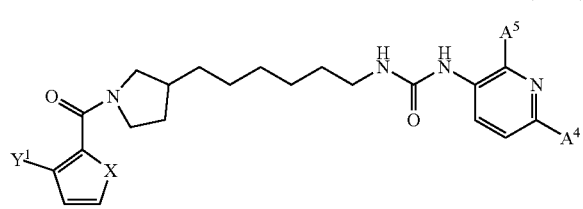

Formula (XXVIII)

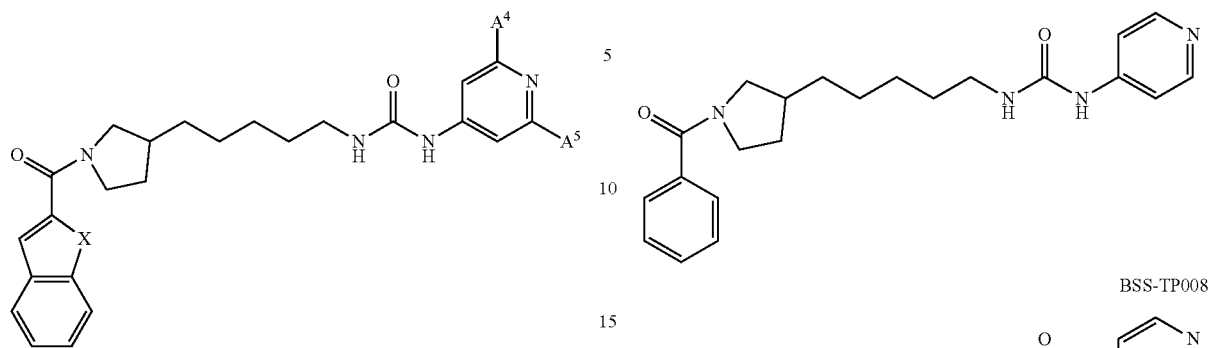

Formula (XXIX)

Formula (XXX)

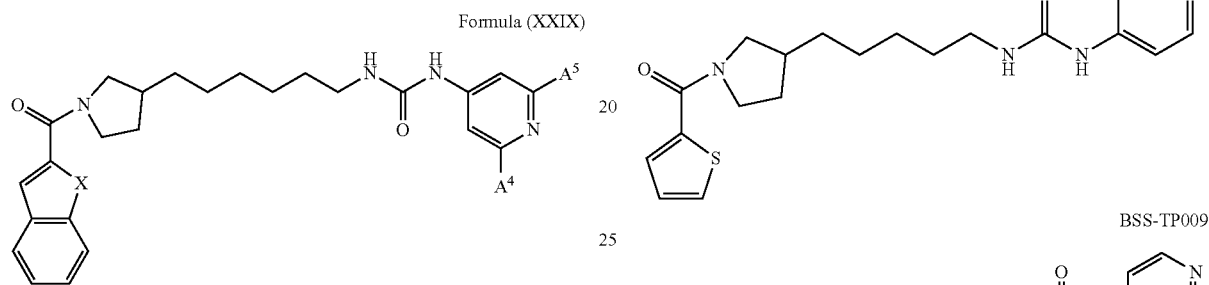

Formula (XXXI)

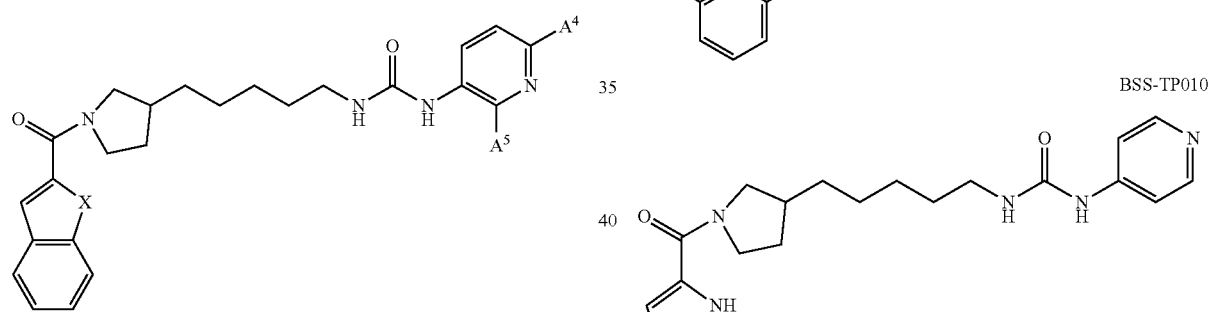

where X is a heteroatom, including nitrogen, oxygen, or sulfur;

$A^4$ is hydrogen, fluoro, chloro, bromo, iodo or hydroxyl; and $A^5$ is hydrogen, fluoro, chloro, bromo, iodo or hydroxyl.

In some embodiments, the pyrrolidine derivative or a pharmaceutically acceptable salt thereof is selected from the following pyrrolidine derivatives or pharmaceutically acceptable salts thereof:

BSS-TP007

BSS-TP008

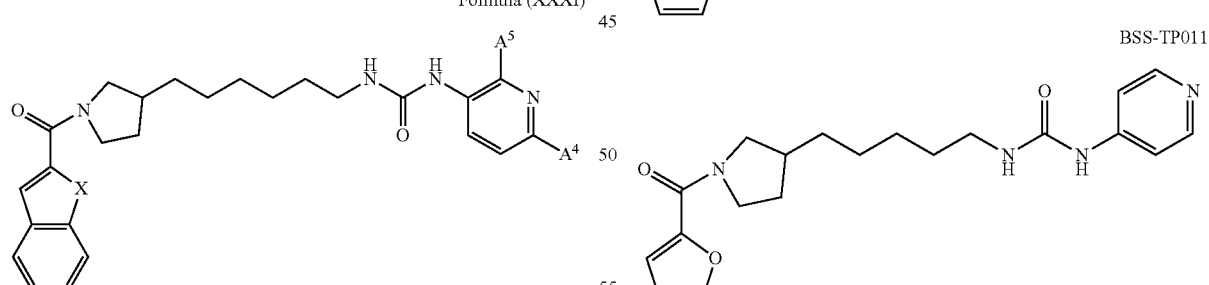

BSS-TP009

BSS-TP010

BSS-TP011

BSS-TP012

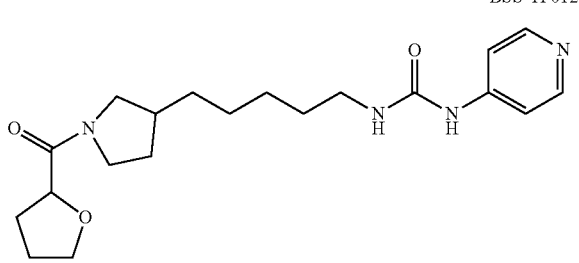

-continued

BSS-TP013

BSS-TP014

BSS-TP0015

BSS-TP016

BSS-TP017

BSS-TP018

-continued

BSS-TP019

BSS-TP020

BSS-TP021

BSS-TP022

BSS-TP023

BSS-TP024
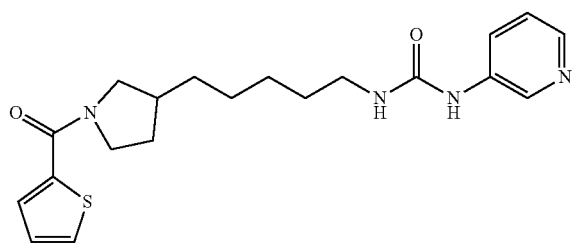
BSS-TP029
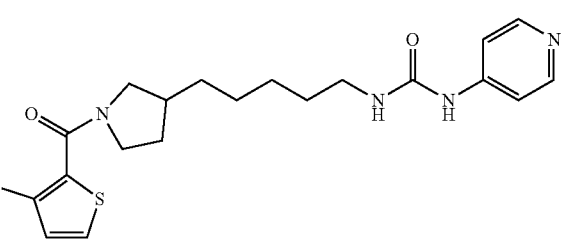
BSS-TP025
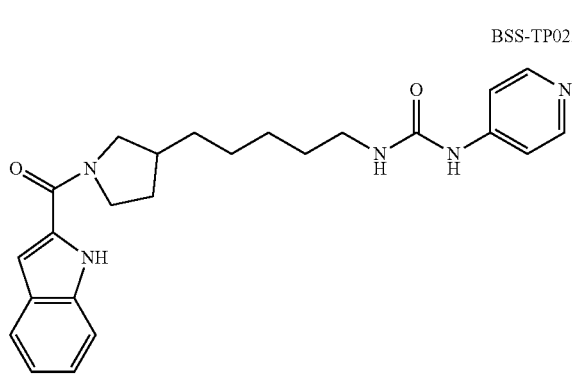
BSS-TP030
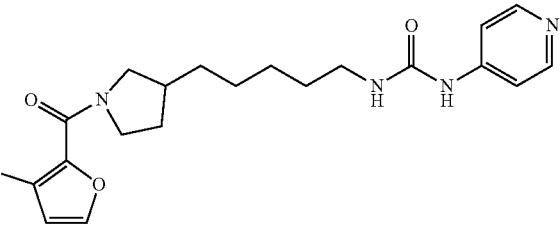
BSS-TP031
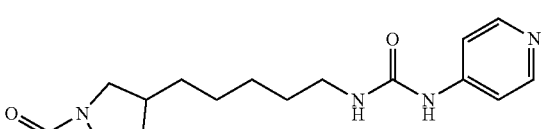
BSS-TP026
BSS-TP032
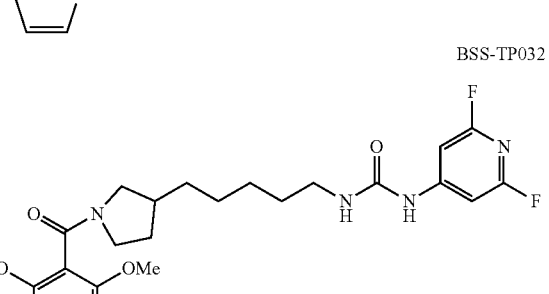
BSS-TP027
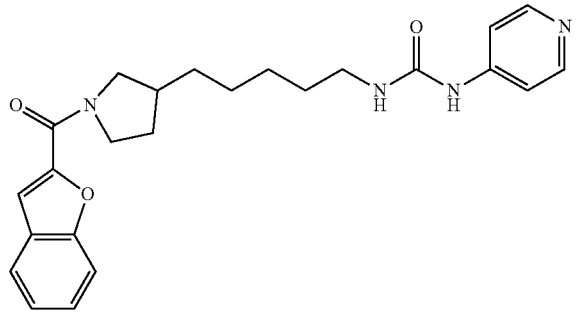
BSS-TP033
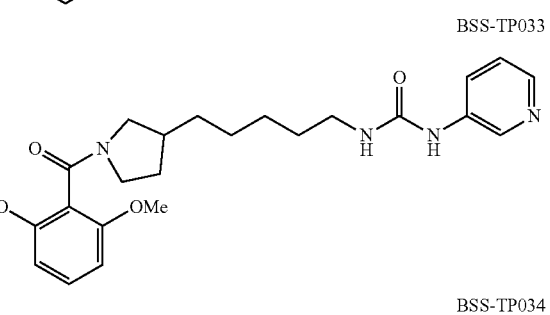
BSS-TP028
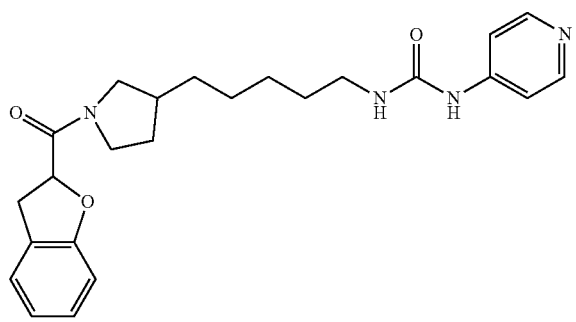
BSS-TP034
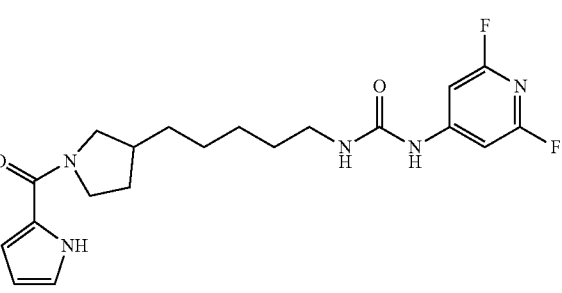

-continued
BSS-TP035
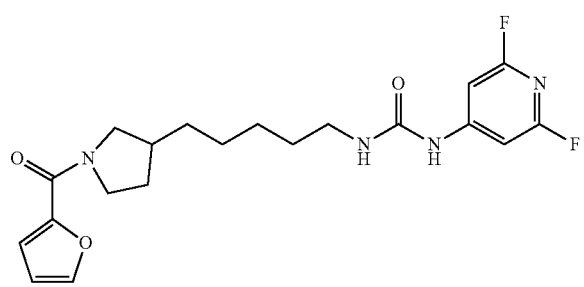
BSS-TP036
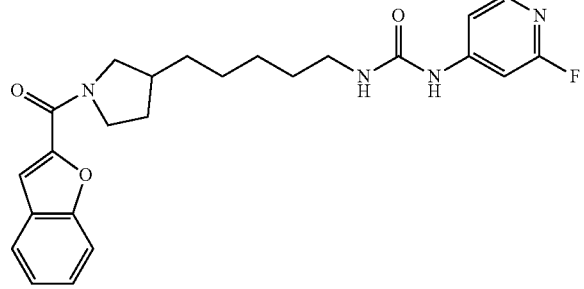
BSS-TP037
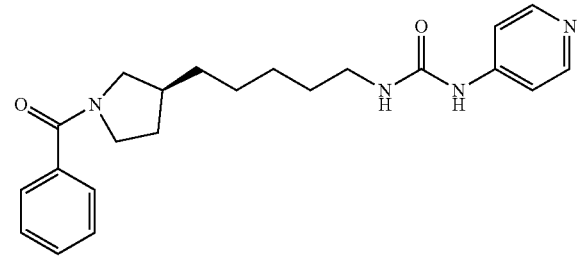
BSS-TP038
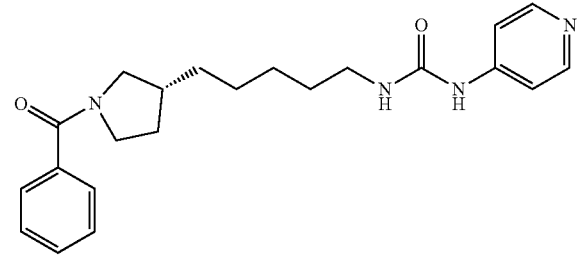
BSS-TP039
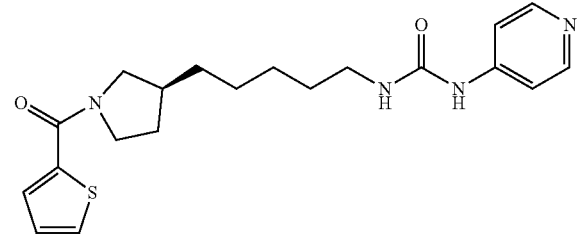
-continued
BSS-TP040
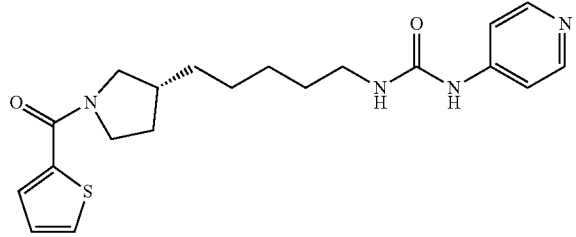
BSS-TP101
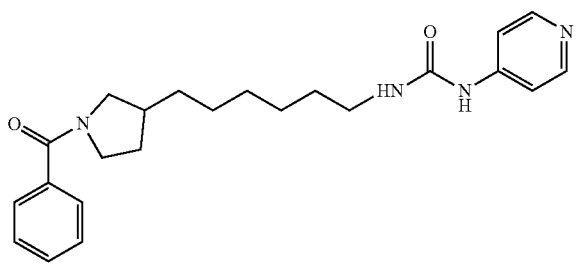
BSS-TP102
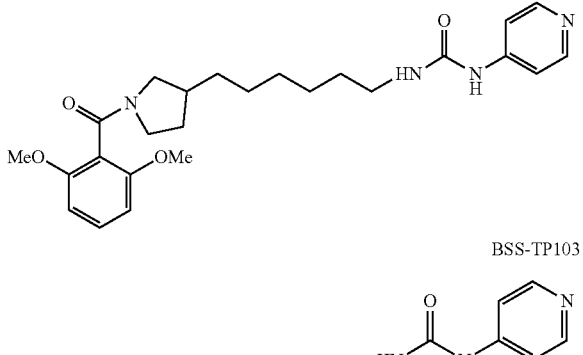
BSS-TP103
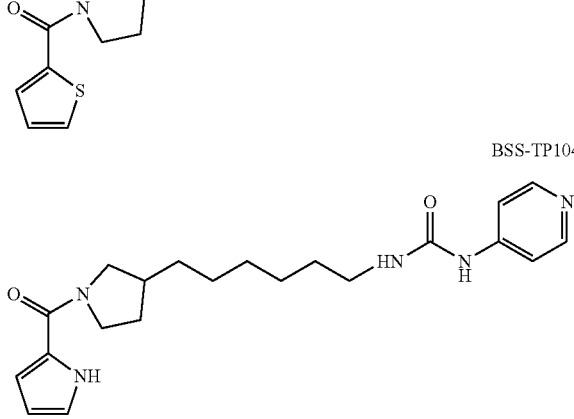
BSS-TP104
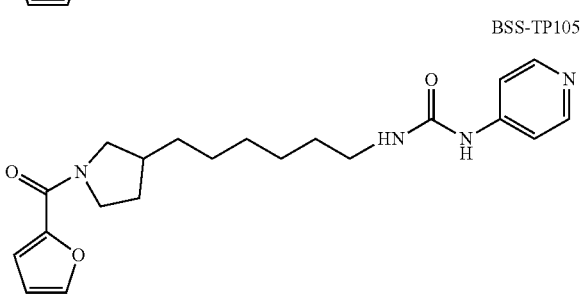
BSS-TP105
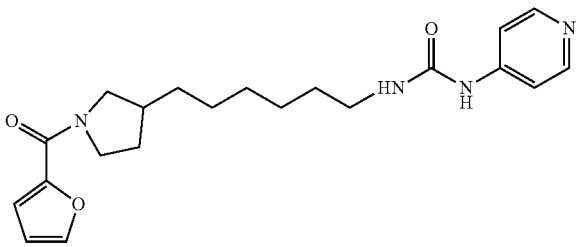

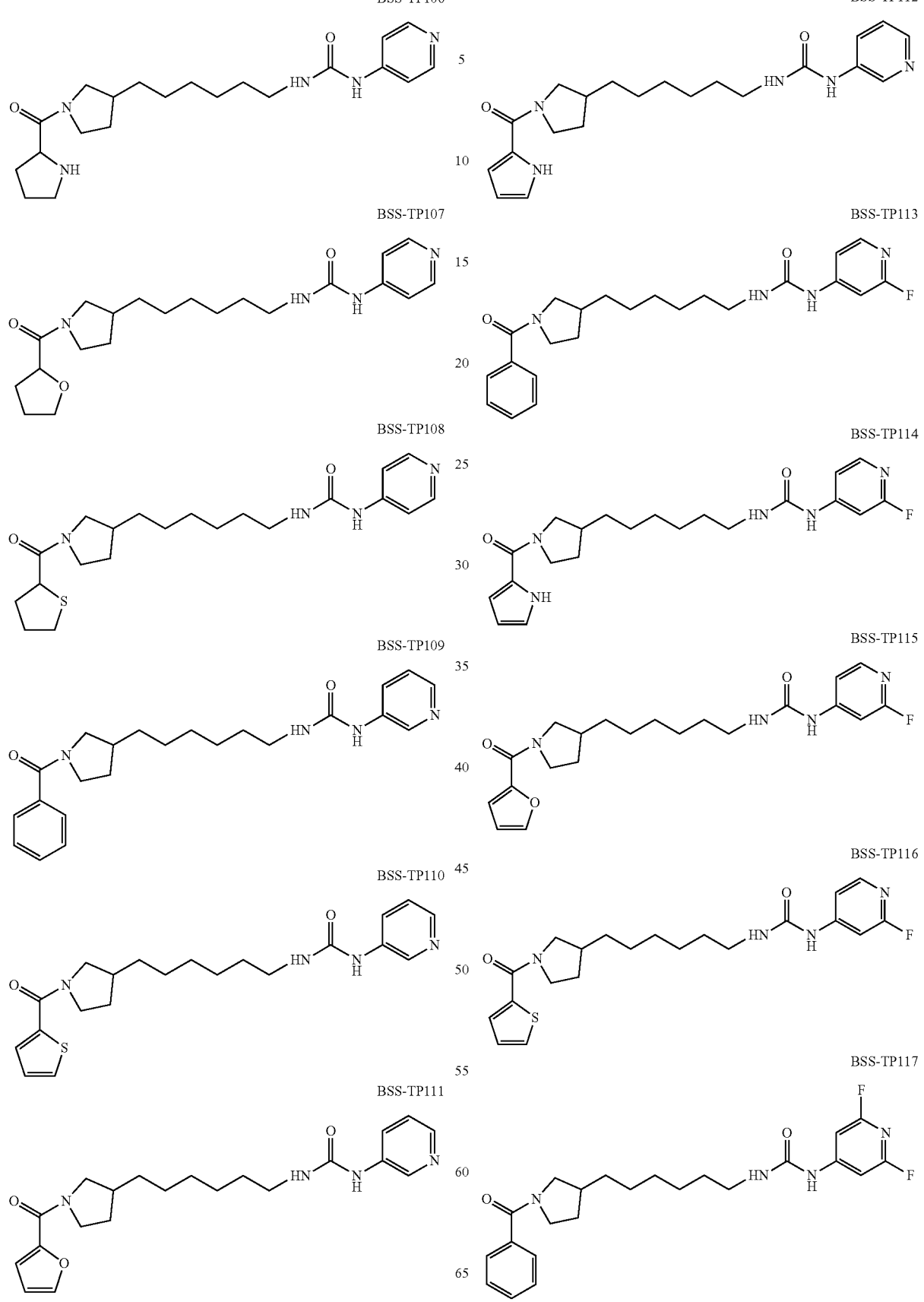

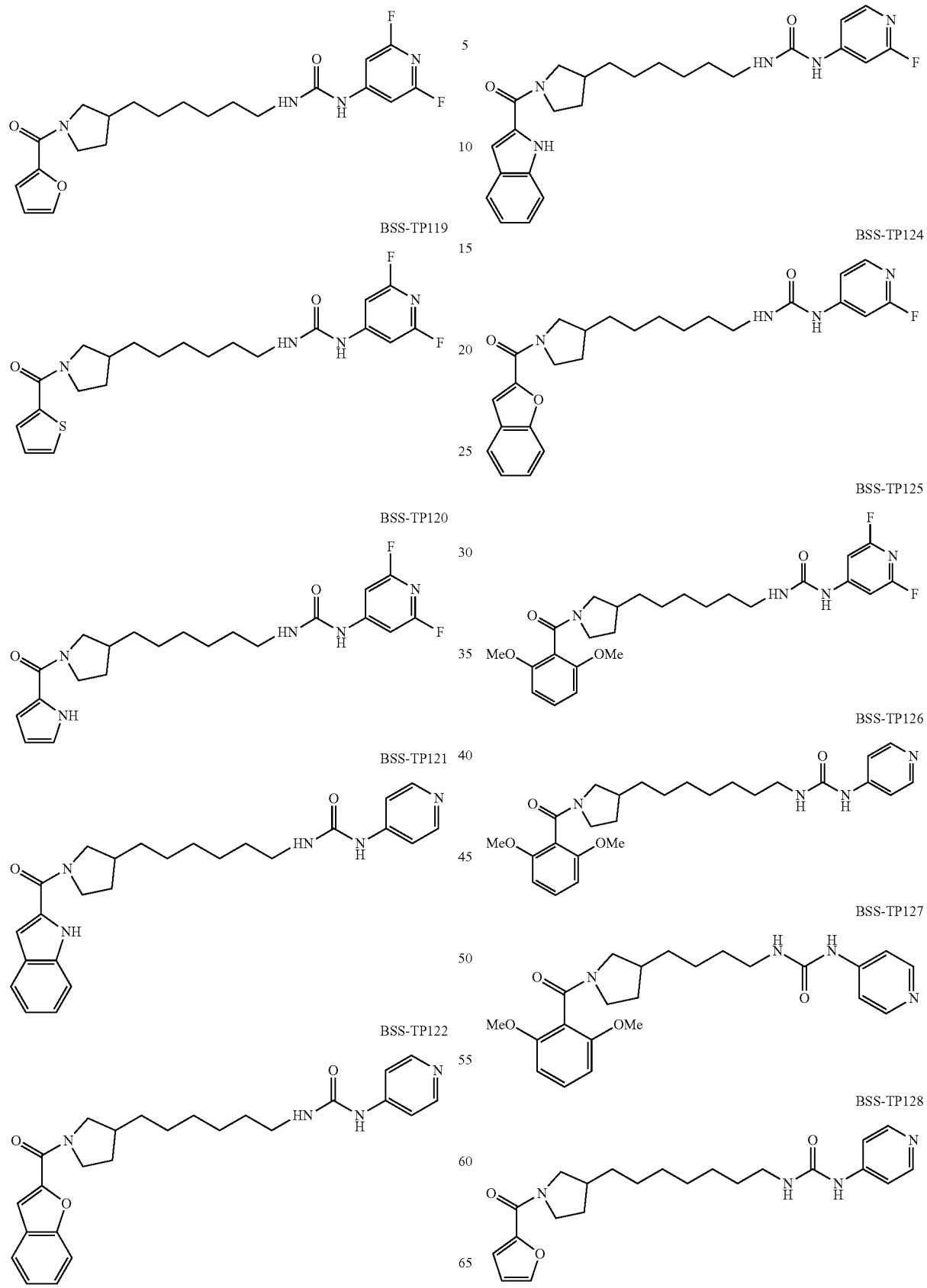

-continued

BSS-TP129
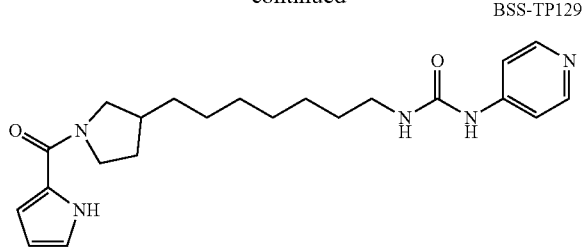

BSS-TP130
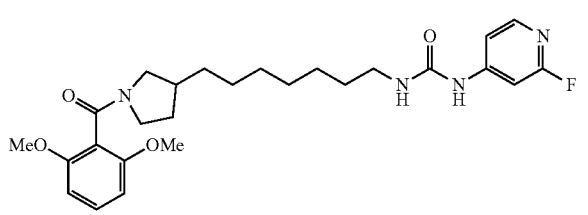

BSS-TP131
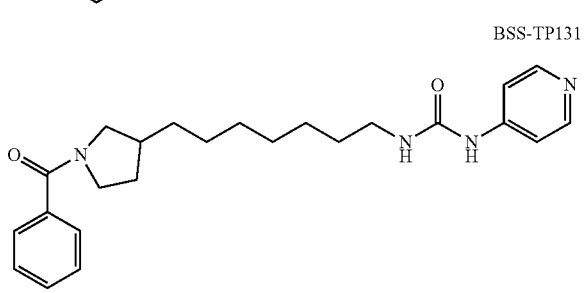

BSS-TP132
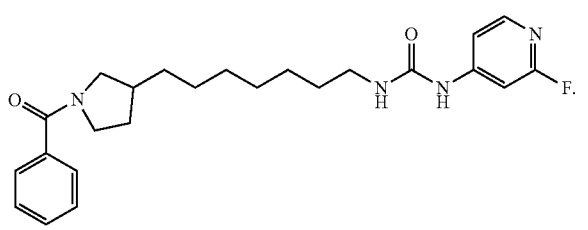

The present invention further provides use of the pyrrolidine derivative or a pharmaceutically acceptable salt thereof in the preparation of drugs for treating diseases associated with abnormal $NAD^+$ expression. The diseases associated with abnormal $NAD^+$ expression includes inflammations, autoimmune diseases, cardiovascular diseases or cancers. The inflammations include osteoarthritis, nephritis or atopic dermatitis; the autoimmune diseases include systemic lupus erythematosus, multiple sclerosis or rheumatoid arthritis; the cardiovascular diseases include atherosclerosis or stroke; and the cancers include breast cancer, prostate cancer, lung cancer, liver cancer, esophageal cancer, gastric cancer, colon cancer, pancreatic cancer or multiple myeloma.

The "pharmaceutically acceptable salt" means a salt that retains the bioavailability and characteristics of the compound of the present invention as a free acid or free base and is obtained by reacting the free acid with a nontoxic inorganic base or organic base or the free base with a nontoxic inorganic acid or organic acid.

The term "optically active isomer" refers to an isomer produced by different spatial arrangement of atoms in a molecule, including cis-trans isomers, enantiomers, diastereomers and conformational isomers.

The present invention has the following beneficial effects.

The present invention relates to a pyrrolidine derivative or its optically active isomer, or a pharmaceutically acceptable salt thereof, which is useful as an NAMPT inhibitor, and useful as a potential agent for the chemotherapy of a variety of diseases associated with abnormal $NAD^+$ expression. The pyrrolidine derivative has pyrrolidine as a parent structure, to which pyridinylurea (or substituted pyridinylurea) is attached by an intermediate aliphatic chain, and a side arylformyl (or heterocyclylformyl) group is attached. This structure is an optimized structure of the NAMPT inhibitor FK866, in which the acrylamido group is replaced by a urea structure, to increases the water solubility of the compound. Moreover, the difficulty in synthesis is reduced accordingly, which is conducive to the subsequent industrial production.

FK866 has a structure shown below:

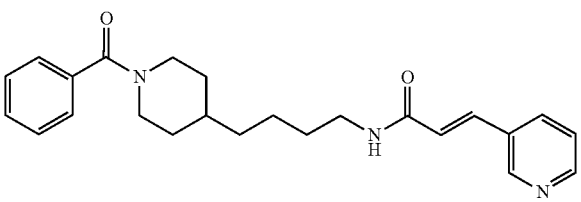 [SMILES: O=C(/C=C/c1cccnc1)NCCCCC1CCN(C(=O)c2ccccc2)CC1]

DETAILED DESCRIPTION

The present invention will be further explained below by way of examples. The following examples are merely used to illustrate the present invention, but not intended to limit the scope of the present invention.

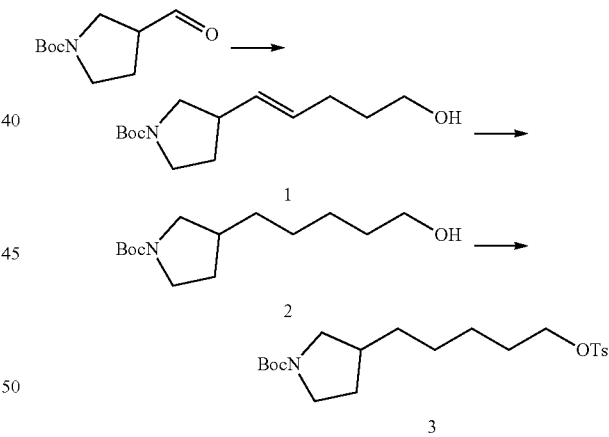

Example 1

2.1 g of triphenylphosphine was dissolved in 20 ml of tetrahydrofuran, and then 2.5 g of 4-bromo-1-butanol was added and refluxed overnight under a nitrogen atmosphere. A large amount of solid was precipitated, which was allowed to stand still. The liquid was poured out, and then the white solid was washed twice with 10 ml of anhydrous tetrahydrofuran. 20 ml of anhydrous tetrahydrofuran was added, and cooled to −10° C. 5.6 ml of a n-butyl lithium solution (2.5 M) was slowly added under a nitrogen atmosphere, during which the temperature was controlled at −5° C. or below. After that, the reaction was further incubated with stirring for 2 hrs, and cooled to −10° C. or below. A solution of 2 g of 1-Boc-3-pyrrolidinylcarboxaldehyde dissolved in 20 ml of anhydrous tetrahydrofuran was added dropwise to the above reaction solution. The reaction was continued at this temperature for 2 hrs, heated to room temperature and stirred overnight. The reaction solution was cooled to 0° C., 10 ml of a saturated ammonium chloride solution was added dropwise, and 20 ml of water was added. The organic layer was separated, and the aqueous layer was extracted twice with 30 ml of ethyl acetate. The organic layers were combined, and washed sequentially with a saturate sodium chloride solution and water. The organic layer was dried over anhydrous sodium sulfate, concentrated under reduce pressure, and separated by column chromatography (ethyl acetate EA/petroleum ether PE=1:10-1:1 vol/vol, gradient elution), to obtain 2.3 g of an oily product 1-Boc-3-(5'-hydroxy-1'-en-pentyl) pyrrolidine (1).

Example 2

0.5 g of 1-Boc-3-(5'-hydroxy-1'-en-pentyl)pyrrolidine (1) was dissolved in 10 ml of methanol, and then 0.025 g of Pd/C (5%) was added and heated to 40° C. The reaction was continued under a hydrogen atmosphere (4 atm) for 48 hrs, and then the reaction solution was filtered. The filtrate was concentrated under reduce pressure, and separated by column chromatography (EA/PE vol/vol=1:1-10:1, gradient elution) to obtain 0.45 g of an oily product 1-Boc-3-(5'-hydroxy-1'-pentyl)pyrrolidine (2).

Example 3

0.45 g of 1-Boc-3-(5'-hydroxy-1'-pentyl)pyrrolidine (2) was dissolved in 10 ml of dichloromethane, and then cooled to 0° C. 1.5 ml of triethyl amine was added. A solution of 1.2 g of p-toluenesulfonyl chloride dissolved in 6 ml of dichloromethane was added dropwise under a nitrogen atmosphere, and reacted overnight with stirring. A saturated ammonium chloride solution was added. The organic layer was separated, and then the aqueous layer was extracted with 10 ml of dichloromethane. The organic layers were combined, dried over anhydrous sodium sulfate, and filtered. The filtrate was concentrated under reduce pressure, and separated by column chromatography (EA/PE=1:4 vol/vol), to obtain 0.51 g of an oily product 1-Boc-3-(5'-p-toluenesulfonyl-1'-pentyl)pyrrolidine (3).

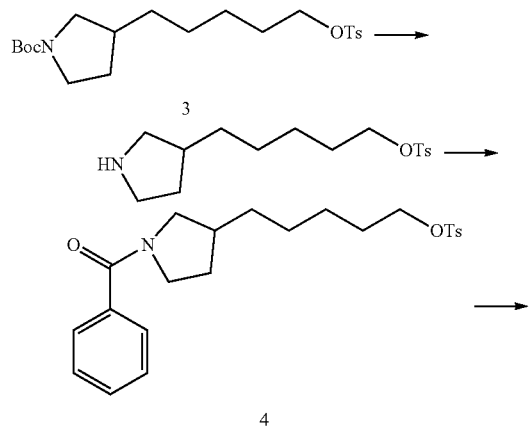

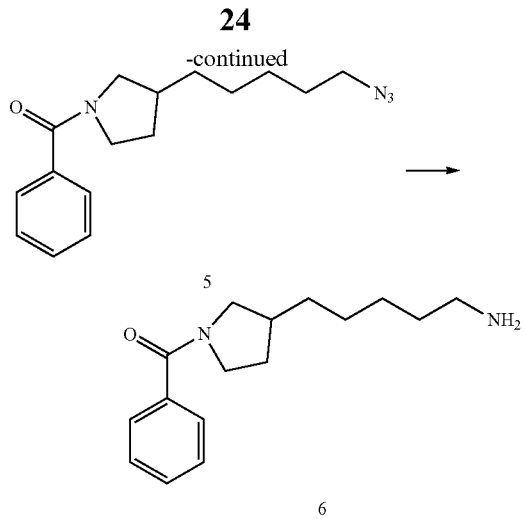

Example 4

0.5 g of 1-Boc-3-(5'-p-toluenesulfonyl-1'-pentyl)pyrrolidine (3) was dissolved in 10 ml of dichloromethane, and then 2 ml of trifluoroacetic acid was added, stirred overnight at room temperature and concentrated under reduced pressure. 10 ml of dichloromethane was added, and then 1 ml of triethyl amine was added dropwise and cooled to 0° C. Under a nitrogen atmosphere, 1.2 g of benzoyl chloride was added, and reacted overnight with stirring. A saturated ammonium chloride solution was added. The organic layer was separated, and then the aqueous layer was extracted with 10 ml of dichloromethane. The organic layers were combined, dried over anhydrous sodium sulfate, and filtered. The filtrate was concentrated under reduce pressure, and separated by column chromatography (EA/P=1:2-2:1 vol/vol, gradient elution), to obtain 0.43 g of an oily product 1-benzoyl-3-(5'-p-toluenesulfonyl-1'-pentyl)pyrrolidine (4).

Example 5

0.39 g of 1-benzoyl-3-(5'-p-toluenesulfonyl-1'-pentyl) pyrrolidine (4) was dissolved in 4 ml of N,N-dimethyl formamide (DMF), and then 0.15 g of sodium azide was added, heated to 70° C. and reacted overnight. After concentration under reduced pressure, 10 ml of dichloromethane was added, and washed sequentially with water and a saturated sodium chloride solution. The reaction solution was concentrated under reduced pressure, and separated by column chromatography (EA/PE=1:4-1:1 vol/vol, gradient elution), to obtain 0.24 g of an oily product 1-benzoyl-3-(5'-azido-1'-pentyl)pyrrolidine (5).

Example 6

0.18 g of 1-benzoyl-3-(5'-azido-1'-pentyl)pyrrolidine (5) was dissolved in 5 ml of tetrahydrofuran, and then 0.15 g of triphenylphosphine and 2 drops of water were added and refluxed overnight. After concentration under reduced pressure, 10 ml of dichloromethane was added, and washed sequentially with water and a saturated sodium chloride solution. The reaction solution was concentrated under reduced pressure, and separated by column chromatography (dichloromethane/methanol/aqueous ammonia=10:1:0.1 vol/vol/vol), to obtain 0.16 g of an oily product 1-benzoyl-3-(5'-amino-1'-pentyl)pyrrolidine (6), LCMS: 261[M+H].

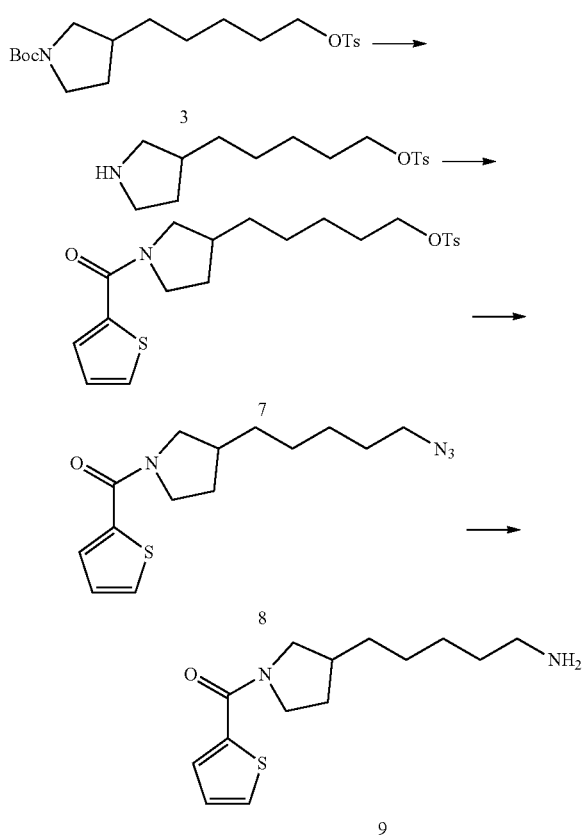

Example 7

0.5 g of 1-Boc-3-(5'-p-toluenesulfonyl-1'-pentyl)pyrrolidine (3) was dissolved in 10 ml of dichloromethane, and then 2 ml of trifluoroacetic acid was added, stirred overnight at room temperature and concentrated under reduced pressure. 10 ml of dichloromethane was added, and then 1 ml of triethyl amine was added dropwise and cooled to 0° C. Under nitrogen atmosphere, 1.5 g of 2-thienylformyl chloride was added, and reacted overnight with stirring. A saturated ammonium chloride solution was added. The organic layer was separated, and then the aqueous layer was extracted with 10 ml of dichloromethane. The organic layers were combined, dried over anhydrous sodium sulfate, and filtered. The filtrate was concentrated under reduce pressure, and separated by column chromatography (EA/PE vol/vol=1:2-2:1, gradient elution), to obtain 0.41 g of an oily product 1-(2-thienylformyl)-3-(5'-p-toluenesulfonyl-1'-pentyl)pyrrolidine (7).

Example 8

0.41 g of 1-(2-thienylformyl)-3-(5'-p-toluenesulfonyl-1'-pentyl)pyrrolidine (7) was dissolved in 4 ml of DMF, and then 0.15 g of sodium azide was added, heated to 70° C. and reacted overnight. After concentration under reduced pressure, 10 ml of dichloromethane was added, and washed sequentially with water and a saturated sodium chloride solution. The reaction solution was concentrated under reduced pressure, and separated by column chromatography (EA/PE vol/vol=1:4-1:1, gradient elution), to obtain 0.25 g of an oily product 1-(2-thienylformyl)-3-(5'-azido-1'-pentyl)pyrrolidine (8).

Example 9

0.21 g of 1-(2-thienylformyl)-3-(5'-azido-1'-pentyl)pyrrolidine (8) was dissolved in 5 ml of tetrahydrofuran, 0.15 g of triphenylphosphine and 2 drops of water were added and refluxed overnight. After concentration under reduced pressure, 10 ml of dichloromethane was added, and washed sequentially with water and a saturated sodium chloride solution. The reaction solution was concentrated under reduced pressure, and separated by column chromatography (dichloromethane/methanol/aqueous ammonia=10:1:0.1 vol/vol/vol), to obtain 0.18 g of an oily product 1-(2-thienylformyl)-3-(5'-amino-1'-pentyl)pyrrolidine (9). LCMS: 267 [M+H].

The following compounds can be prepared according to the above method of preparing the compound 6 and the compound 9 starting from the compound 3:

| Preparation number | Name of Compound | Structure | MS (m/z) |
|---|---|---|---|
| 10 | 1-(2,6-dimethoxybenzoyl)-3-(5'-amino-1'-pentyl)pyrrolidine | 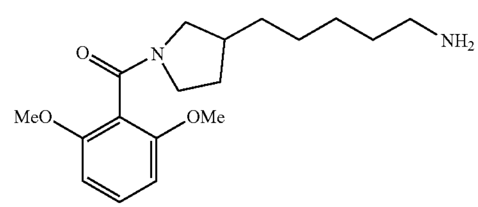 [SMILES: COc1cccc(OC)c1C(=O)N1CCC(CCCCCN)C1] | 321 (M + 1) |
| 10-1 | 1-(2,6-dimethoxybenzoyl)-3-(6'-amino-1'-hexyl)pyrrolidine | 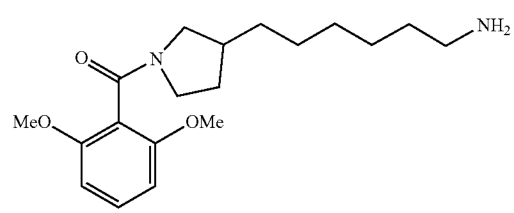 [SMILES: COc1cccc(OC)c1C(=O)N1CCC(CCCCCCN)C1] | 335 (M + 1) |

-continued

| Preparation number | Name of Compound | Structure | MS (m/z) |
|---|---|---|---|
| 10-2 | 1-(2,6-dimethoxybenzoyl)-3-(7'-amino-1'-heptyl)pyrrolidine | 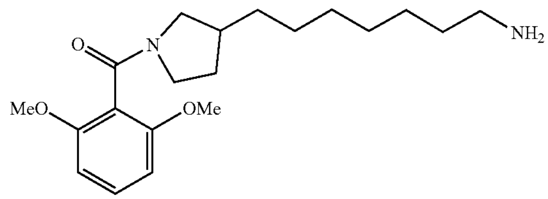 [SMILES: COc1cccc(OC)c1C(=O)N1CCC(CCCCCCCN)C1] | 349 (M + 1) |
| 10-3 | 1-(2,6-dimethoxybenzoyl)-3-(4'-amino-1'-butyl)pyrrolidine | 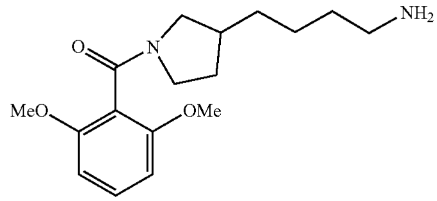 [SMILES: COc1cccc(OC)c1C(=O)N1CCC(CCCCN)C1] | 307 (M + 1) |
| 10-4 | 1-benzoyl-3-(6'-amino-1'-hexyl)pyrrolidine | 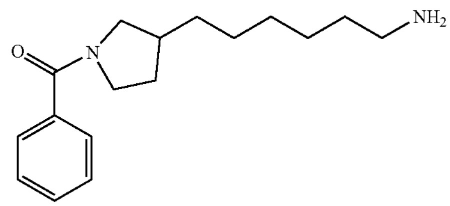 [SMILES: NCCCCCCC1CCN(C(=O)c2ccccc2)C1] | 275 (M + 1) |
| 10-5 | 1-benzoyl-3-(7'-amino-1'-heptyl)pyrrolidine | 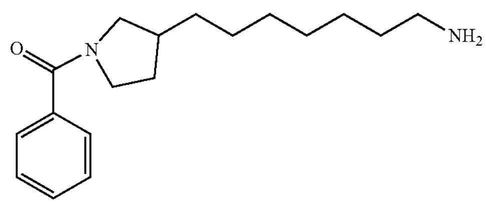 [SMILES: NCCCCCCCC1CCN(C(=O)c2ccccc2)C1] | 289 (M + 1) |
| 11 | 1-furoyl-3-(5'-amino-1'-pentyl)pyrrolidine | 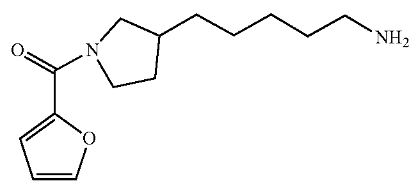 [SMILES: NCCCCCC1CCN(C(=O)c2ccco2)C1] | 251 (M + 1) |
| 11-1 | 1-furoyl-3-(6'-amino-1'-hexyl)pyrrolidine | 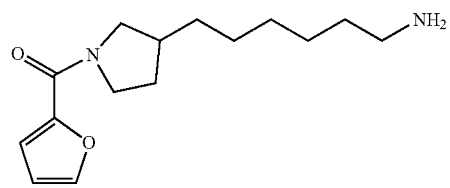 [SMILES: NCCCCCCC1CCN(C(=O)c2ccco2)C1] | 265 (M + 1) |
| 11-2 | 1-furoyl-3-(7'-amino-1'-heptyl)pyrrolidine | 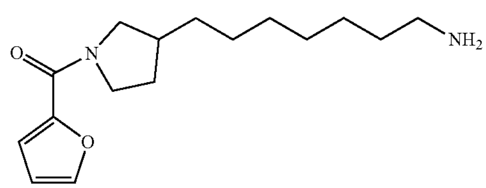 [SMILES: NCCCCCCCC1CCN(C(=O)c2ccco2)C1] | 279 (M + 1) |
| 11-3 | 1-(2-thienylformyl)-3-(6'-amino-1'-hexyl)pyrrolidine | 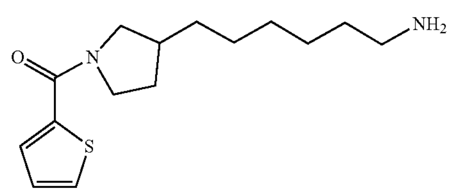 [SMILES: NCCCCCCC1CCN(C(=O)c2cccs2)C1] | 281 (M + 1) |

| Preparation number | Name of Compound | Structure | MS (m/z) |
|---|---|---|---|
| 12 | 1-(2-pyrroloylformyl)-3-(5'-amino-1'-pentyl)pyrrolidine | 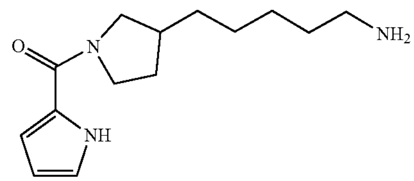 [SMILES: NCCCCCC1CCN(C(=O)c2ccc[nH]2)C1] | 250 (M + 1) |
| 12-1 | 1-(2-pyrrolylformyl)-3-(6'-amino-1'-hexyl)pyrrolidine | 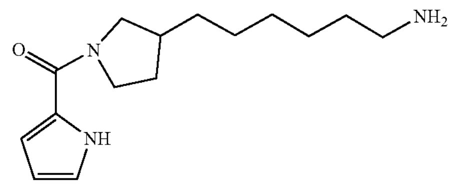 [SMILES: NCCCCCCC1CCN(C(=O)c2ccc[nH]2)C1] | 264 (M + 1) |
| 12-2 | 1-(2-pyrrolylformyl)-3-(7'-amino-1'-heptyl)pyrrolidine | 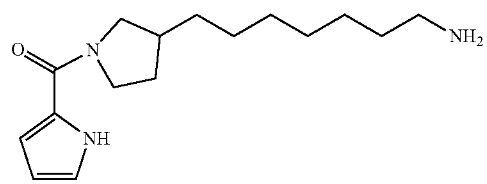 [SMILES: NCCCCCCCC1CCN(C(=O)c2ccc[nH]2)C1] | 278 (M + 1) |
| 13 | 1-(2-pyrrolidinylformyl)-3-(5'-amino-1'-pentyl)pyrrolidine | 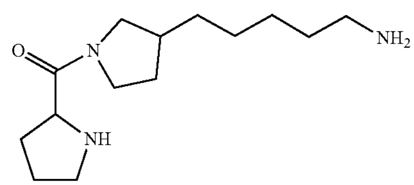 [SMILES: NCCCCCC1CCN(C(=O)C2CCCN2)C1] | 254 (M + 1) |
| 14 | 1-(2-tetrahydrofurylformyl)-3-(5'-amino-1'-pentyl)pyrrolidine | 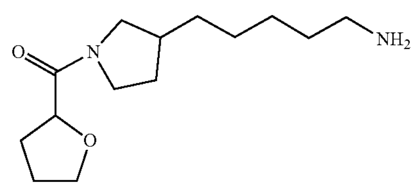 [SMILES: NCCCCCC1CCN(C(=O)C2CCCO2)C1] | 255 (M + 1) |
| 15 | 1-(2-tetrahydrothienylformyl)-3-(5'-amino-1'-pentyl)pyrrolidine | 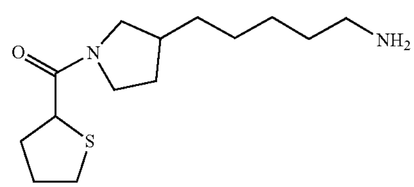 [SMILES: NCCCCCC1CCN(C(=O)C2CCCS2)C1] | 271 (M + 1) |
| 15-1 | 1-(2-tetrahydrothienylformyl)-3-(6'-amino-1'-hexyl)pyrrolidine | 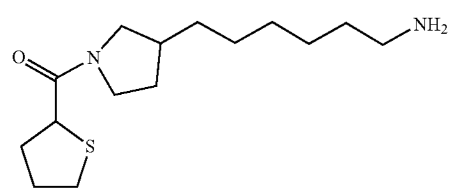 [SMILES: NCCCCCCC1CCN(C(=O)C2CCCS2)C1] | 285 (M + 1) |
| 15-2 | 1-(2-pyrrolidinylformyl)-3-(6'-amino-1'-hexyl)pyrrolidine | 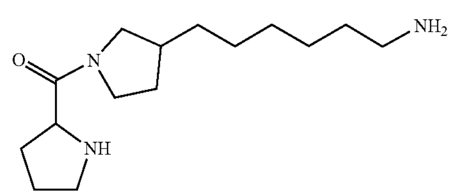 [SMILES: NCCCCCCC1CCN(C(=O)C2CCCN2)C1] | 268 (M + 1) |

-continued

| Preparation number | Name of Compound | Structure | MS (m/z) |
|---|---|---|---|
| 15-3 | 1-(2-tetrahydrofurylformyl)-3-(6'-amino-1'-hexyl)pyrrolidine | 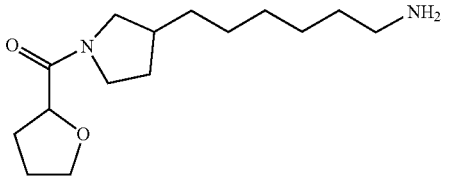 [SMILES: NCCCCCCC1CCN(C(=O)C2CCCO2)C1] | 269 (M + 1) |
| 15-4 | 1-(3-fluoro-2-thienylformyl)-3-(5'-amino-1'-pentyl)pyrrolidine | 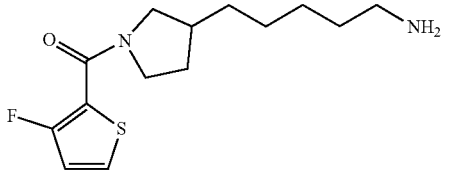 [SMILES: NCCCCCC1CCN(C(=O)c2sccc2F)C1] | 285 (M + 1) |
| 15-5 | 1-(3-fluoro-2-pyrrolylformyl)-3-(5'-amino-1'-pentyl)pyrrolidine | 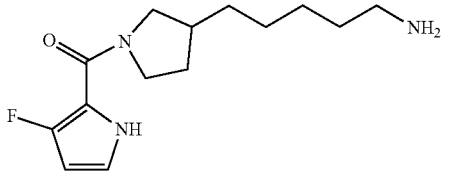 [SMILES: NCCCCCC1CCN(C(=O)c2[nH]ccc2F)C1] | 268 (M + 1) |
| 15-6 | 1-(3-fluoro-2-furylformyl)-3-(5'-amino-1'-pentyl)pyrrolidine | 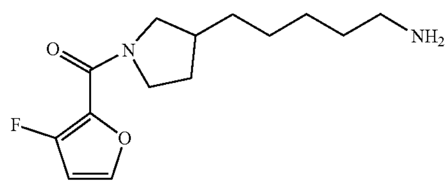 [SMILES: NCCCCCC1CCN(C(=O)c2occc2F)C1] | 269 (M + 1) |
| 16 | 1-(2-indolylformyl)-3-(5'-amino-1'-pentyl)pyrrolidine | 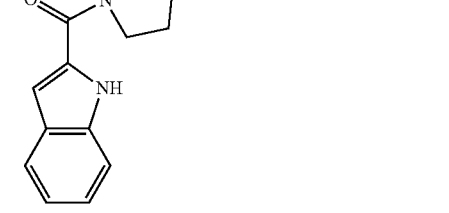 | 300 (M + 1) |
| 16-1 | 1-(2-indolylformyl)-3-(6'-amino-1'-hexyl)pyrrolidine | 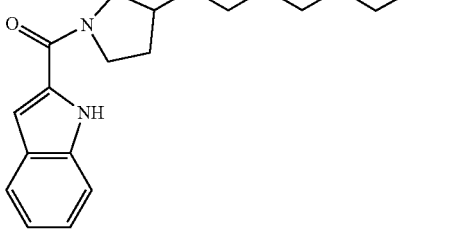 | 314 (M + 1) |
| 17 | 1-(2-benzofurylformyl)-3-(5'-amino-1'-pentyl)pyrrolidine | 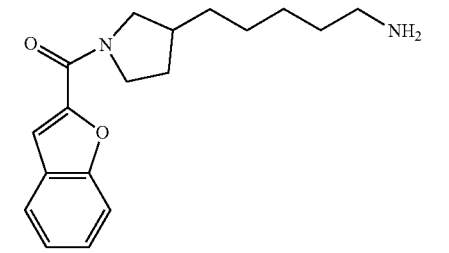 [SMILES: NCCCCCC1CCN(C(=O)c2cc3ccccc3o2)C1] | 301 (M + 1) |

-continued

| Preparation number | Name of Compound | Structure | MS (m/z) |
|---|---|---|---|
| 17-1 | 1-(2-benzofurylformyl)-3-(6'-amino-1'-hexyl)pyrrolidine | 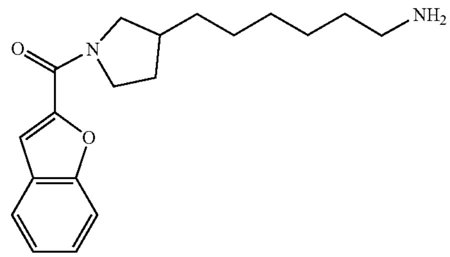 [SMILES: NCCCCCCC1CCN(C(=O)c2cc3ccccc3o2)C1] | 315 (M + 1) |
| 17-2 | 1-(2-benzotetrahydrofurylfuryl)-3-(5'-amino-1'-pentyl)pyrrolidine | 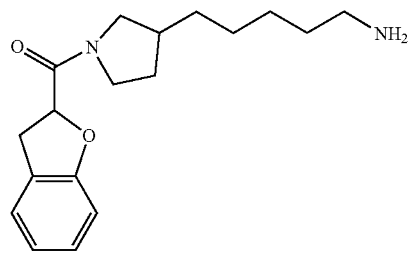 [SMILES: NCCCCCC1CCN(C(=O)C2Cc3ccccc3O2)C1] | 303 (M + 1) |

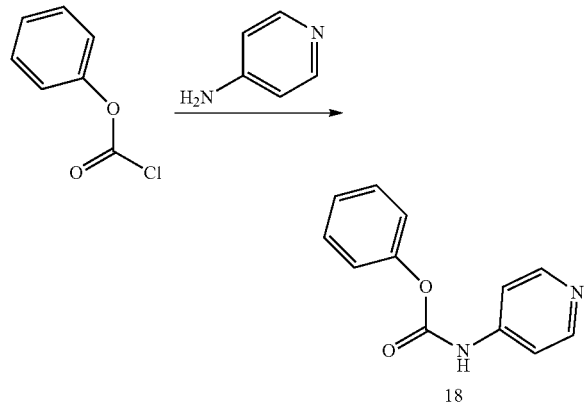

Example 10

In an ice-water bath, 4-aminopyridine (0.96 g, 10.24 mmol) was added in batches to a solution of phenyl chloroformate (1.75 g, 11.2 mmol) and triethyl amine (1.46 g, 14.4 mmol) in dichloromethane (30 ml), gradually warmed to room temperature and stirred for 16 hrs. The system was washed with a saturated aqueous NaHCO$_3$ solution (50 ml). The organic layer was separated, and the aqueous layer was extracted with CH$_2$Cl$_2$ (20 ml×3). The organic layers were combined, washed with brine (50 ml), dried (Na$_2$SO$_4$), filtered, and concentrated under reduced pressure, to obtain phenyl 4-pyridinylaminoformate (18) as a white solid powder (1.95 mg, 90%), 1H NMR (CDCl$_3$) δ 7.22-7.18 (d, 2H), 7.26-7.31 (m, 1H), 7.36 (brs, 1H), 7.36-7.47 (m, 4H), 8.49-8.55 (d, 2H), LCMS: 215[M+H].

The following compounds can be prepared according to the method in Example 10:

| Preparation number | Name of Compound | Structure | MS (m/z) |
|---|---|---|---|
| 18-1 | Phenyl 3-pyridinylaminoformate | 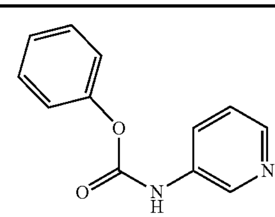 | 215 (M + 1) |
| 18-2 | Phenyl 3-fluoro-4-pyridinylaminoformate | 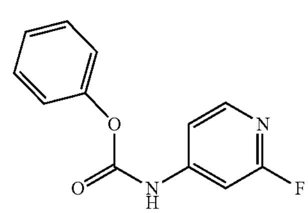 [SMILES: O=C(Nc1ccnc(F)c1)Oc1ccccc1] | 233 (M + 1) |

-continued

| Preparation number | Name of Compound | Structure | MS (m/z) |
|---|---|---|---|
| 18-3 | Phenyl 3,5-difluoro-4-pyridinylaminoformate | 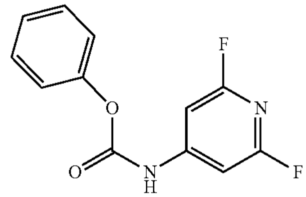 [SMILES: O=C(Nc1cc(F)nc(F)c1)Oc1ccccc1] | 251 (M + 1) |

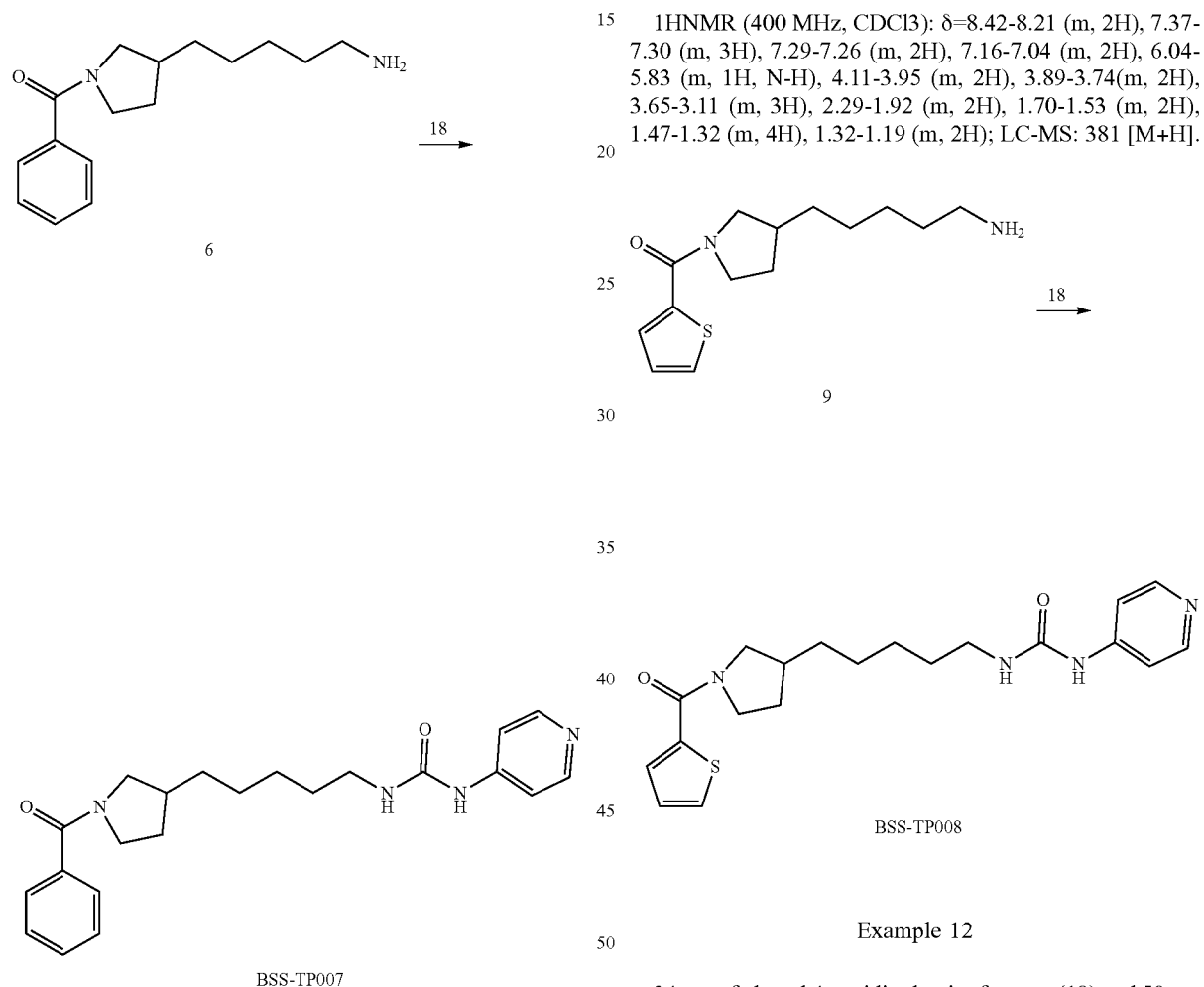

1HNMR (400 MHz, CDCl3): δ=8.42-8.21 (m, 2H), 7.37-7.30 (m, 3H), 7.29-7.26 (m, 2H), 7.16-7.04 (m, 2H), 6.04-5.83 (m, 1H, N-H), 4.11-3.95 (m, 2H), 3.89-3.74(m, 2H), 3.65-3.11 (m, 3H), 2.29-1.92 (m, 2H), 1.70-1.53 (m, 2H), 1.47-1.32 (m, 4H), 1.32-1.19 (m, 2H); LC-MS: 381 [M+H].

Example 11

36 mg of phenyl 4-pyridinylaminoformate (18) and 51 mg of 1-benzoyl-3-(5'-amino-1'-pentyl)pyrrolidine (6) were dissolved in 5 ml of acetonitrile, 20.8 μl of triethyl amine was added and stirred overnight at 30° C. (30 hrs). The reaction solution was concentrated under reduced pressure, and directly separated by column chromatography (dichloromethane/methanol vol/vol=10:1-5:1, gradient elution), to obtain about 45 mg of a sticky target compound BSS-TP007 1-(5-(1-(benzoyl)pyrrolidin-3-yl)pentyl)-2-(4-pyridinyl) urea.

Example 12

34 mg of phenyl 4-pyridinylaminoformate (18) and 50 mg of 1-(2-thienylformyl)-3-(5'-amino-1'-pentyl)pyrrolidine (9) were dissolved in 5 ml of acetonitrile, 22 μl of triethyl amine was added, and stirred overnight at 30° C. (30 hrs). The reaction solution was concentrated under reduced pressure, and directly separated by column chromatography (dichloromethane/methanol vol/vol=10:1-5:1, gradient elution), to obtain about 40 mg of a sticky target compound BSS-TP008 1-(5-(1-(2-thienylformyl)pyrrolidin-3 -yl)pentyl)-2-(4-pyridinyl)urea.

1HNMR (400 MHz, CDCl3): δ=8.60-8.31 (m, 2H), 7.46-7.42 (1H), 7.30-7.18 (m, 3H), 7.07-7.01 (m, 1H), 6.09-5.99 (m, 1H, N-H), 4.09-3.92 (m, 2H), 3.88-3.73(m, 2H), 3.60-3.15 (m, 3H), 2.32-1.95 (m, 2H), 1.67-1.51 (m, 2H), 1.49-1.29 (m, 4H), 1.33-1.18 (m, 2H); LC-MS: 387[M+H].

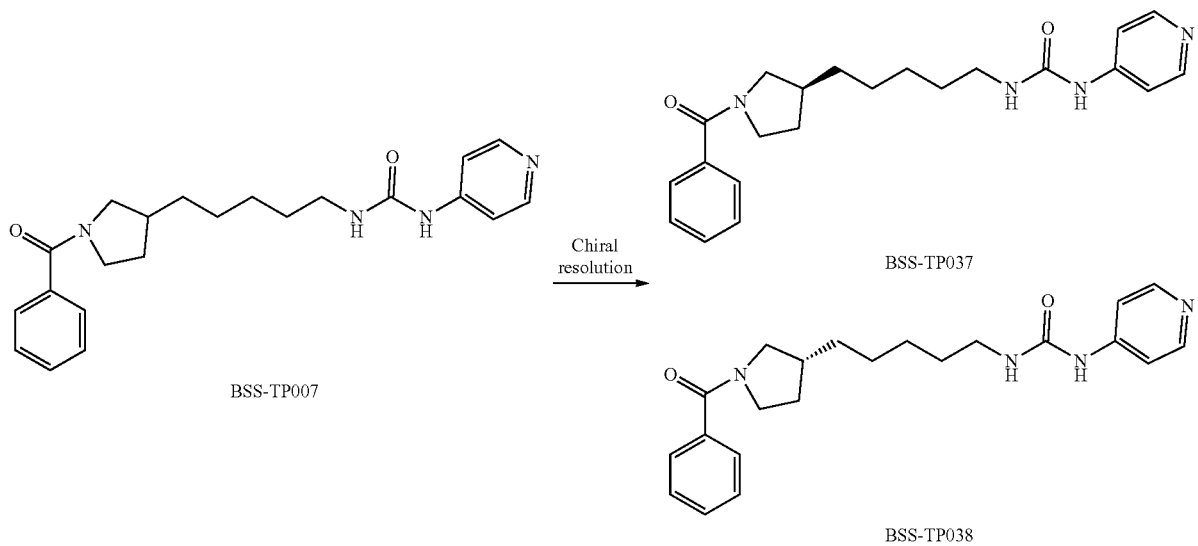

Example 13

The compound BSS-TP007 was resolved by chiral liquid column chromatography to obtain the compound BSS-TP037 (ee%>99%, chiral HPLC, mobile phase: n-hexane/ethanol=90/10 vol/vol, column temperature: 35° C.; flow rate: 0.8 mL/min, detection wavelength: 227 nm, retention time: 14.32 min) and BSS-TP038 (ee%>99%, chiral HPLC, mobile phase: n-hexane/ethanol=90/10 vol/vol, column temperature: 35° C.; flow rate: 0.8 mL/min, detection wavelength: 227 nm, retention time: 18.76 min).

BSS-TP037:1HNMR (400 MHz, CDCl3): δ=8.42-8.21 (m, 2H), 7.37-7.30 (m, 3H), 7.29-7.26 (m, 2H), 7.16-7.04 (m, 2H), 6.04-5.83 (m, 1H, N-H), 4.11-3.95 (m, 2H), 3.89-3.74(m, 2H), 3.65-3.11 (m, 3H), 2.29-1.92 (m, 2H), 1.70-1.53 (m, 2H), 1.47-1.32 (m, 4H), 1.32-1.19 (m, 2H); LC-MS:381 [M+H];

BSS-TP038:1HNMR (400 MHz, CDCl3): δ=8.42-8.21 (m, 2H), 7.37-7.30 (m, 3H), 7.29-7.26 (m, 2H), 7.16-7.04 (m, 2H), 6.04-5.83 (m, 1H, N-H), 4.11-3.95 (m, 2H), 3.89-3.74(m, 2H), 3.65-3.11 (m, 3H), 2.29-1.92 (m, 2H), 1.70-1.53 (m, 2H), 1.47-1.32 (m, 4H), 1.32-1.19 (m, 2H); LC-MS:381 [M+H].

The following compounds can be prepared according to the above method of preparing the compound BSS-TP007 starting from the compounds 6 and 18:

| Preparation number | Name of Compound | Structure | MS (m/z) |
| --- | --- | --- | --- |
| BSS-TP009 | 1-(5-(1-(2,6-dimethoxybenzoyl)pyrrolidin-3-yl)pentyl)-2-(4-pyridinyl)urea | 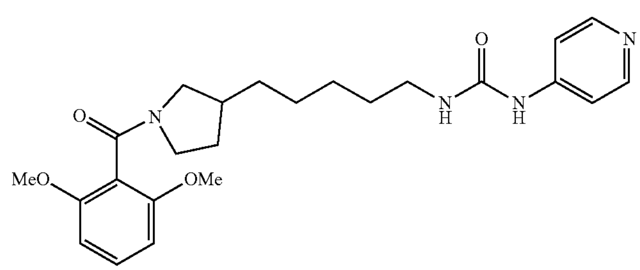 [SMILES: COc1cccc(OC)c1C(=O)N1CCC(CCCCCNC(=O)Nc2ccncc2)C1] | 441 (M + 1) |
| BSS-TP011 | 1-(5-(1-(furoyl)pyrrolidin-3-yl)pentyl)-2-(4-pyridinyl)urea | 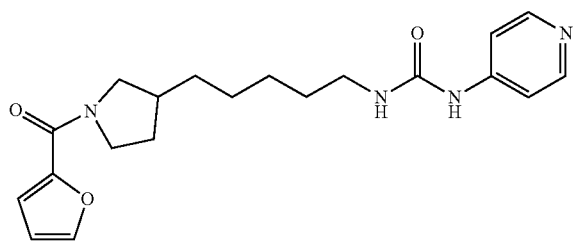 | 371 (M + 1) |

-continued

| Preparation number | Name of Compound | Structure | MS (m/z) |
|---|---|---|---|
| BSS-TP010 | 1-(5-(1-(2-pyrrolylformyl)pyrrolidin-3-yl)pentyl)-2-(4-pyridinyl)urea | 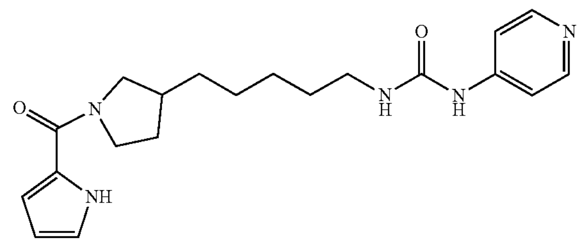 [SMILES: O=C(NCCCCCC1CCN(C(=O)c2ccc[nH]2)C1)Nc1ccncc1] | 370 (M + 1) |
| BSS-TP014 | 1-(5-(1-(2-pyrrolidinylformyl)pyrrolidin-3-yl)pentyl)-2-(4-pyridinyl)urea | 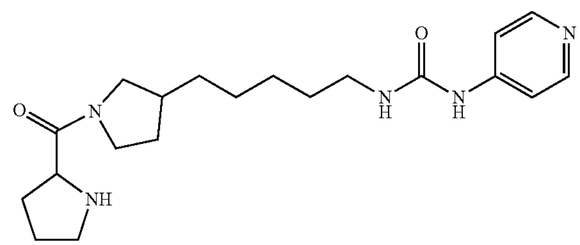 [SMILES: O=C(NCCCCCC1CCN(C(=O)C2CCCN2)C1)Nc1ccncc1] | 374 (M + 1) |
| BSS-TP012 | 1-(5-(1-(2-tetrahydrofurylformyl)pyrrolidin-3-yl)pentyl)-2-(4-pyridinyl)urea | 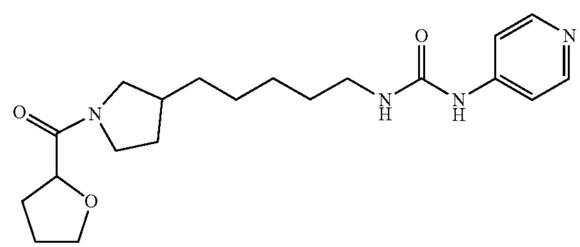 [SMILES: O=C(NCCCCCC1CCN(C(=O)C2CCCO2)C1)Nc1ccncc1] | 375 (M + 1) |
| BSS-TP013 | 1-(5-(1-(2-tetrahydrothienylformyl)pyrrolidin-3-yl)pentyl)-2-(4-pyridinyl)urea | 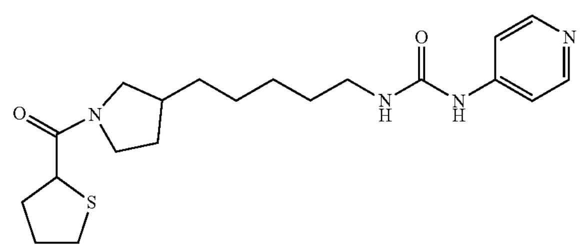 [SMILES: O=C(NCCCCCC1CCN(C(=O)C2CCCS2)C1)Nc1ccncc1] | 391 (M + 1) |
| BSS-TP015 | 1-(5-(1-(benzoyl)pyrrolidin-3-yl)pentyl)-2-(3-fluoro-4-pyridinyl)urea | 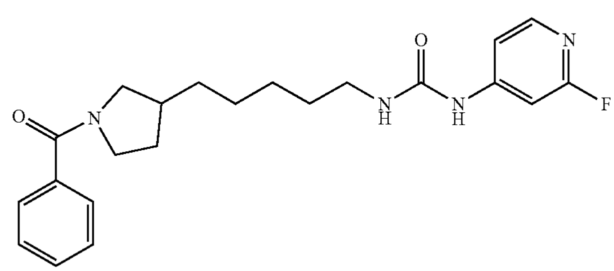 [SMILES: O=C(NCCCCCC1CCN(C(=O)c2ccccc2)C1)Nc1ccnc(F)c1] | 399 (M + 1) |
| BSS-TP016 | 1-(5-(1-(2,6-dimethoxybenzoyl)pyrrolidin-3-yl)pentyl)-2-(3-fluoro-4-pyridinyl)urea | 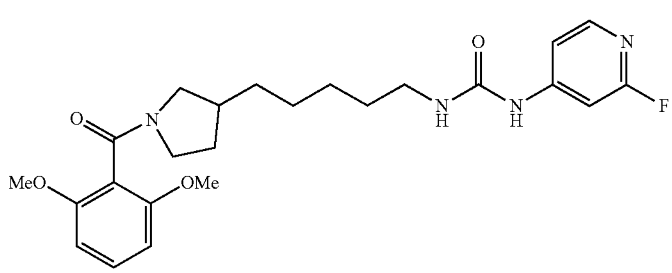 [SMILES: COc1cccc(OC)c1C(=O)N1CCC(CCCCCNC(=O)Nc2ccnc(F)c2)C1] | 459 (M + 1) |

-continued

| Preparation number | Name of Compound | Structure | MS (m/z) |
|---|---|---|---|
| BSS-TP017 | 1-(5-(1-(2-pyrrolylformyl)pyrrolidin-3-yl)pentyl)-2-(3-fluoro-4-pyridinyl)urea | 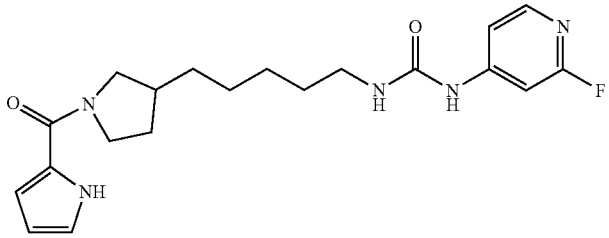 [SMILES: O=C(NCCCCCC1CCN(C(=O)c2ccc[nH]2)C1)Nc1ccnc(F)c1] | 388 (M + 1) |
| BSS-TP018 | 1-(5-(1-(furoyl)pyrrolidin-3-yl)pentyl)-2-(3-fluoro-4-pyridinyl)urea | 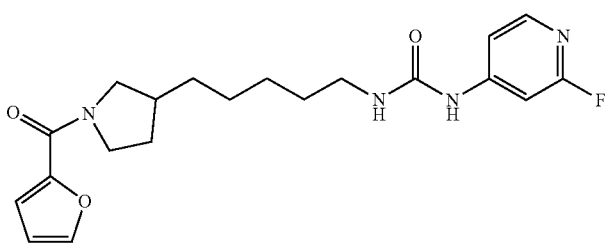 [SMILES: O=C(NCCCCCC1CCN(C(=O)c2ccco2)C1)Nc1ccnc(F)c1] | 389 (M + 1) |
| BSS-TP019 | 1-(5-(1-(2-thienylformyl)pyrrolidin-3-yl)pentyl)-2-(3-fluoro-4-pyridinyl)urea | 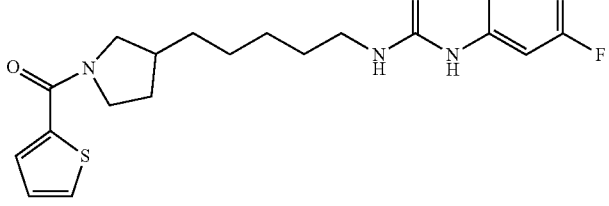 | 405 (M + 1) |
| BSS-TP020 | 1-(5-(1-(2-pyrrolidinylformyl)pyrrolidin-3-yl)pentyl)-2-(3-fluoro-4-pyridinyl)urea | 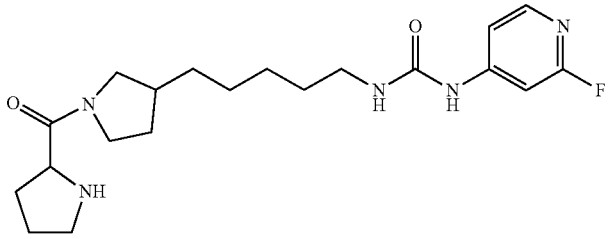 [SMILES: O=C(NCCCCCC1CCN(C(=O)C2CCCN2)C1)Nc1ccnc(F)c1] | 392 (M + 1) |
| BSS-TP021 | 1-(5-(1-(benzoyl)pyrrolidin-3-yl)pentyl)-2-(3,5-difluoro-4-pyridinyl)urea | 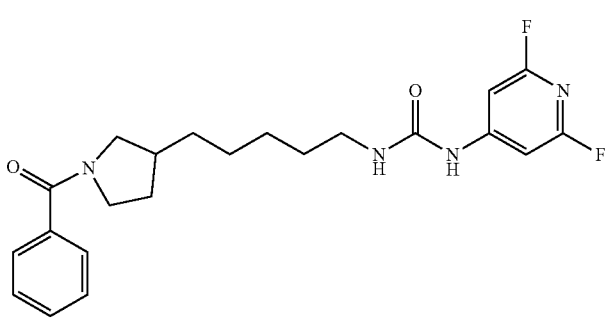 [SMILES: O=C(NCCCCCC1CCN(C(=O)c2ccccc2)C1)Nc1cc(F)nc(F)c1] | 417 (M + 1) |

-continued

| Preparation number | Name of Compound | Structure | MS (m/z) |
|---|---|---|---|
| BSS-TP022 | 1-(5-(1-(2-thienylformyl) pyrrolidin-3-yl)pentyl)-2-(3, 5-difluoro-4-pyridinyl)urea | 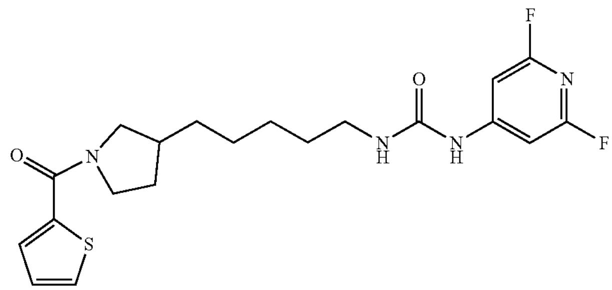 | 423 (M + 1) |
| BSS-TP023 | 1-(5-(1-(benzoyl)pyrrolidin-3-yl)pentyl)-2-(3-pyridinyl)urea | 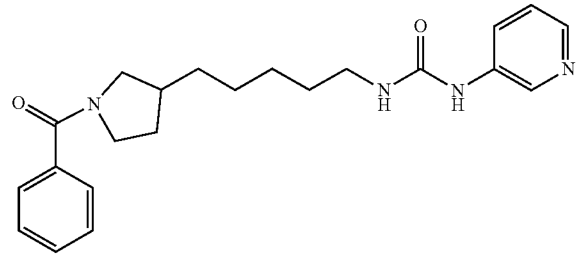 [SMILES: O=C(NCCCCCC1CCN(C(=O)c2ccccc2)C1)Nc1cccnc1] | 381 (M + 1) |
| BSS-TP024 | 1-(5-(1-(2-thienylformyl) pyrrolidin-3-yl)pentyl)-2-(3-pyridinyl)urea | 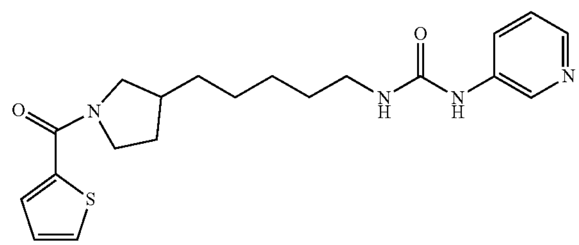 [SMILES: O=C(NCCCCCC1CCN(C(=O)c2cccs2)C1)Nc1cccnc1] | 387 (M + 1) |
| BSS-TP025 | 1-(5-(1-(2-indolylformyl) pyrrolidin-3-yl)pentyl)-2-(4-pyridinyl)urea | 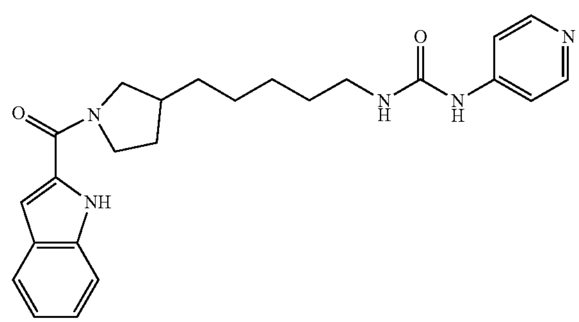 [SMILES: O=C(NCCCCCC1CCN(C(=O)c2cc3ccccc3[nH]2)C1)Nc1ccncc1] | 420 (M + 1) |
| BSS-TP026 | 1-(5-(1-(2-benzofurylformyl) pyrrolidin-3-yl)pentyl)-2-(4-pyridinyl)urea | 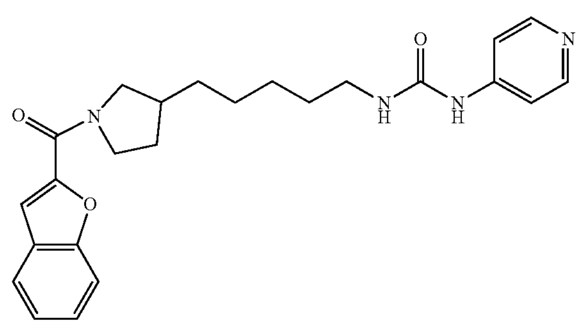 [SMILES: O=C(NCCCCCC1CCN(C(=O)c2cc3ccccc3o2)C1)Nc1ccncc1] | 421 (M + 1) |

-continued

| Preparation number | Name of Compound | Structure | MS (m/z) |
| --- | --- | --- | --- |
| BSS-TP027 | 1-(5-(1-(2-benzotetrahydro furylformyl)pyrrolidin-3-yl) pentyl)-2-(4-pyridinyl)urea | 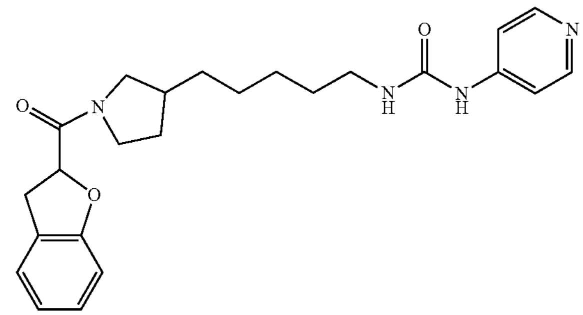 [SMILES: O=C(NCCCCCC1CCN(C(=O)C2Cc3ccccc3O2)C1)Nc1ccncc1] | 423 (M + 1) |
| BSS-TP028 | 1-(5-(1-(furoyl)pyrrolidin-3-yl) pentyl)-2-(3-pyridinyl)urea | 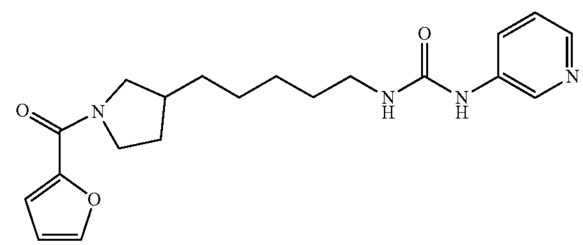 [SMILES: O=C(NCCCCCC1CCN(C(=O)c2ccco2)C1)Nc1cccnc1] | 371 (M + 1) |
| BSS-TP029 | 1-(5-(1-(5-fluoro-2-thienylformyl) pyrrolidin-3-yl)pentyl)-2-(4-pyridinyl)urea | 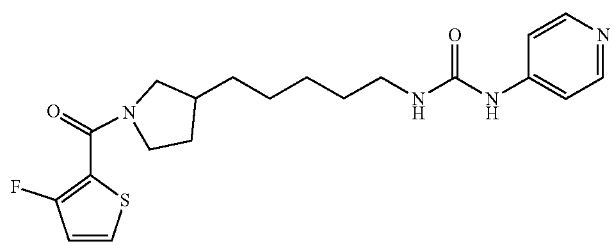 [SMILES: O=C(NCCCCCC1CCN(C(=O)c2sccc2F)C1)Nc1ccncc1] | 405 (M + 1) |
| BSS-TP030 | 1-(5-(1-(5-fluoro-furoyl) pyrrolidin-3-yl)pentyl)-2-(4-pyridinyl)urea | 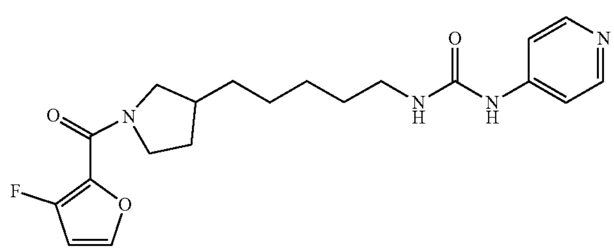 [SMILES: O=C(NCCCCCC1CCN(C(=O)c2occc2F)C1)Nc1ccncc1] | 389 (M + 1) |
| BSS-TP031 | 1-(5-(1-(5-fluoro-2-pyrrolyl formyl)pyrrolidin-3-yl)pentyl)-2-(4-pyridinyl)urea | 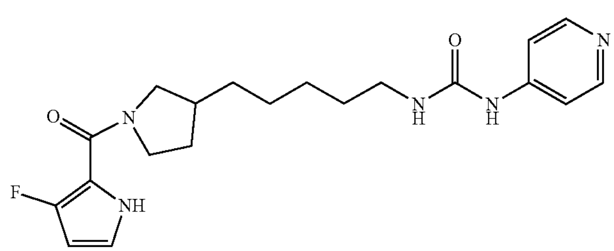 [SMILES: O=C(NCCCCCC1CCN(C(=O)c2[nH]ccc2F)C1)Nc1ccncc1] | 388 (M + 1) |

-continued

| Preparation number | Name of Compound | Structure | MS (m/z) |
|---|---|---|---|
| BSS-TP032 | 1-(5-(1-(2, 6-dimethoxybenzoyl)pyrrolidin-3-yl)pentyl)-2-(3, 5-difluoro-4-pyridinyl)urea | 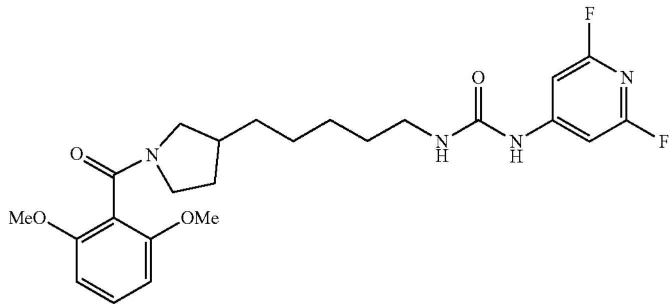 [SMILES: COc1cccc(OC)c1C(=O)N1CCC(CCCCCNC(=O)Nc2cc(F)nc(F)c2)C1] | 477 (M + 1) |
| BSS-TP033 | 1-(5-(1-(2, 6-dimethoxybenzoyl)pyrrolidin-3-yl)pentyl)-2-(3-pyridinyl)urea | 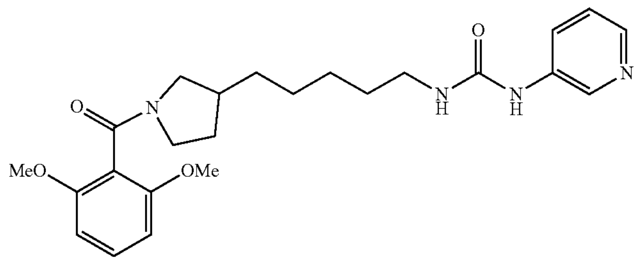 [SMILES: COc1cccc(OC)c1C(=O)N1CCC(CCCCCNC(=O)Nc2cccnc2)C1] | 441 (M + 1) |
| BSS-TP034 | 1-(5-(1-(2-pyrrolylformyl)pyrrolidin-3-yl)pentyl)-2-(3, 5-difluoro-4-pyridinyl)urea | 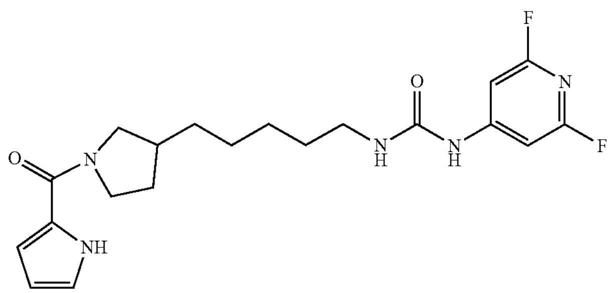 [SMILES: O=C(NCCCCCC1CCN(C(=O)c2ccc[nH]2)C1)Nc1cc(F)nc(F)c1] | 406 (M + 1) |
| BSS-TP035 | 1-(5-(1-(furoyl)pyrrolidin-3-yl)pentyl)-2-(3, 5-difluoro-4-pyridinyl)urea | 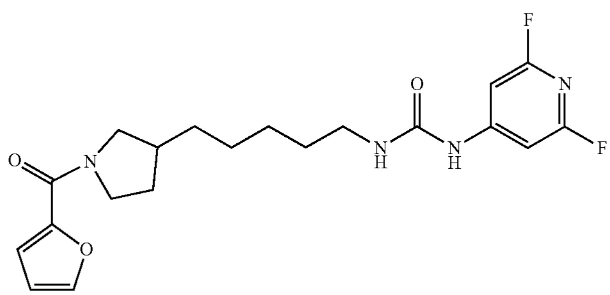 [SMILES: O=C(NCCCCCC1CCN(C(=O)c2ccco2)C1)Nc1cc(F)nc(F)c1] | 407 (M + 1) |
| BSS-TP036 | 1-(5-(1-(2-benzofurylformyl)pyrrolidin-3-yl)pentyl)-2-(3, 5-difluoro-4-pyridinyl)urea | 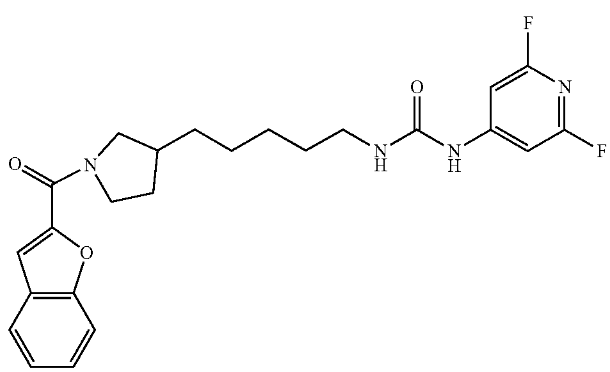 [SMILES: O=C(NCCCCCC1CCN(C(=O)c2cc3ccccc3o2)C1)Nc1cc(F)nc(F)c1] | 457 (M + 1) |

-continued

| Preparation number | Name of Compound | Structure | MS (m/z) |
|---|---|---|---|
| BSS-TP039 | (S)-1-(5-(1-(2-thienylformyl)pyrrolidin-3-yl)pentyl)-2-(4-pyridinyl)urea | 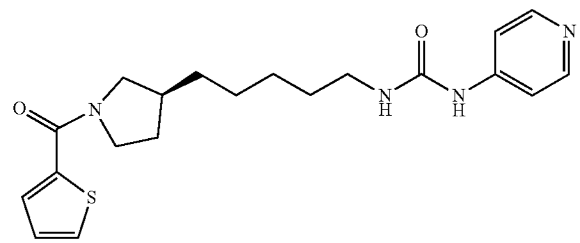 [SMILES: O=C(NCCCCC[C@H]1CCN(C(=O)c2cccs2)C1)Nc1ccncc1] | 387 (M + 1) |
| BSS-TP040 | (R)-1-(5-(1-(2-thienylformyl)pyrrolidin-3-yl)pentyl)-2-(4-pyridinyl)urea | 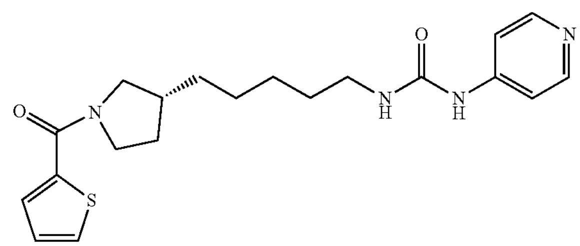 [SMILES: O=C(NCCCCC[C@@H]1CCN(C(=O)c2cccs2)C1)Nc1ccncc1] | 387 (M + 1) |
| BSS-TP101 | 1-(6-(1-(benzoyl)pyrrolidin-3-yl)hexyl)-2-(4-pyridinyl)urea | 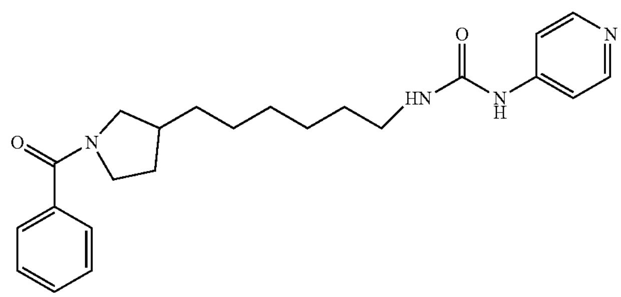 [SMILES: O=C(NCCCCCCC1CCN(C(=O)c2ccccc2)C1)Nc1ccncc1] | 395 (M + 1) |
| BSS-TP102 | 1-(6-(1-(2,6-dimethoxybenzoyl)pyrrolidin-3-yl)hexyl)-2-(4-pyridinyl)urea | 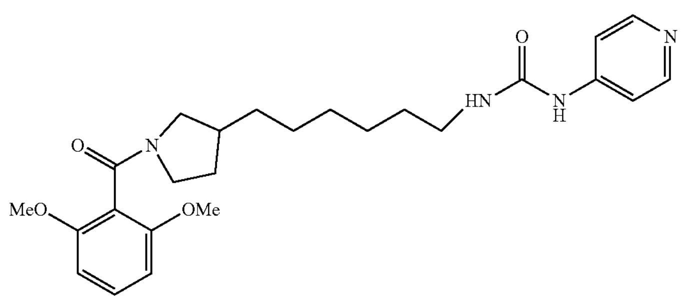 [SMILES: COc1cccc(OC)c1C(=O)N1CCC(CCCCCCNC(=O)Nc2ccncc2)C1] | 455 (M + 1) |
| BSS-TP103 | 1-(6-(1-(2-thienylformyl)pyrrolidin-3-yl)hexyl)-2-(4-pyridinyl)urea | 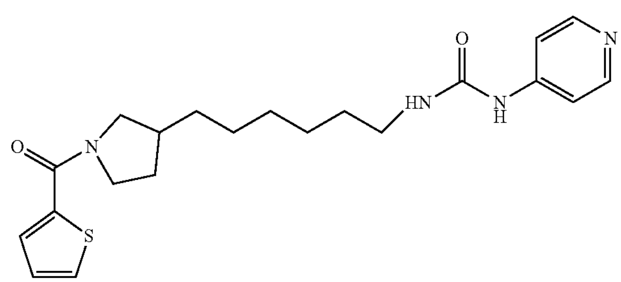 [SMILES: O=C(NCCCCCCC1CCN(C(=O)c2cccs2)C1)Nc1ccncc1] | 401 (M + 1) |

| Preparation number | Name of Compound | Structure | MS (m/z) |
|---|---|---|---|
| BSS-TP104 | 1-(6-(1-(2-pyrrolylformyl)pyrrolidin-3-yl)hexyl)-2-(4-pyridinyl)urea | 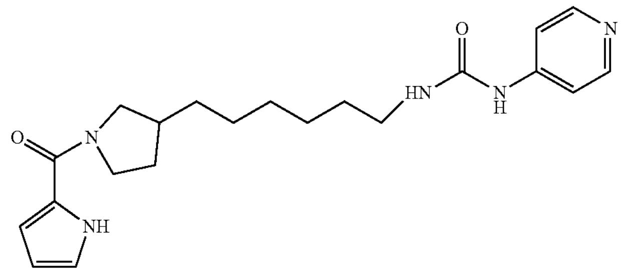 [SMILES: O=C(NCCCCCCC1CCN(C(=O)c2ccc[nH]2)C1)Nc1ccncc1] | 384 (M + 1) |
| BSS-TP105 | 1-(6-(1-(furoyl)pyrrolidin-3-yl)hexyl)-2-(4-pyridinyl)urea | 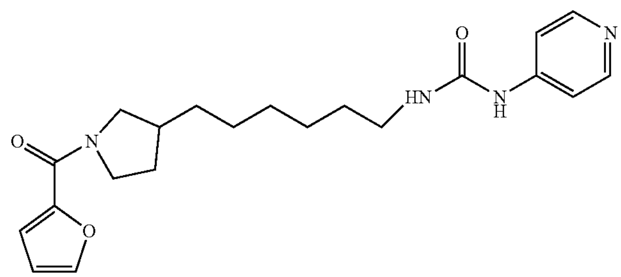 [SMILES: O=C(NCCCCCCC1CCN(C(=O)c2ccco2)C1)Nc1ccncc1] | 385 (M + 1) |
| BSS-TP106 | 1-(6-(1-(2-pyrrolidinylformyl)pyrrolidin-3-yl)hexyl)-2-(4-pyridinyl)urea | 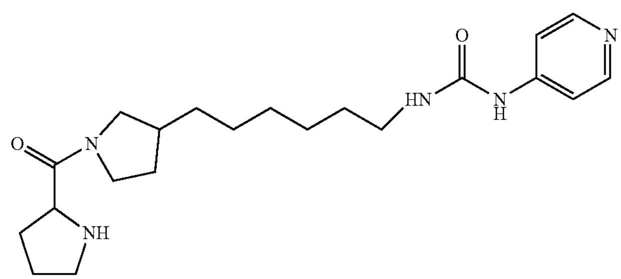 [SMILES: O=C(NCCCCCCC1CCN(C(=O)C2CCCN2)C1)Nc1ccncc1] | 388 (M + 1) |
| BSS-TP107 | 1-(6-(1-(2-tetrahydrofurylformyl)pyrrolidin-3-yl)hexyl)-2-(4-pyridinyl)urea | 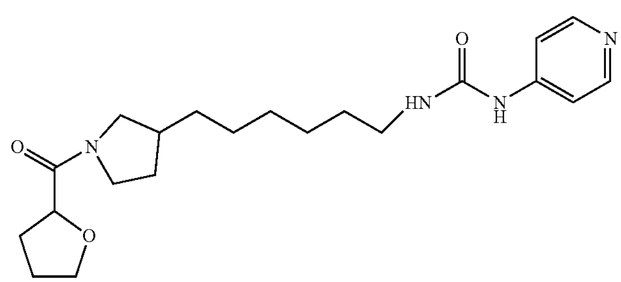 [SMILES: O=C(NCCCCCCC1CCN(C(=O)C2CCCO2)C1)Nc1ccncc1] | 389 (M + 1) |
| BSS-TP108 | 1-(6-(1-(2-tetrahydrothienylformyl)pyrrolidin-3-yl)hexyl)-2-(4-pyridinyl)urea | 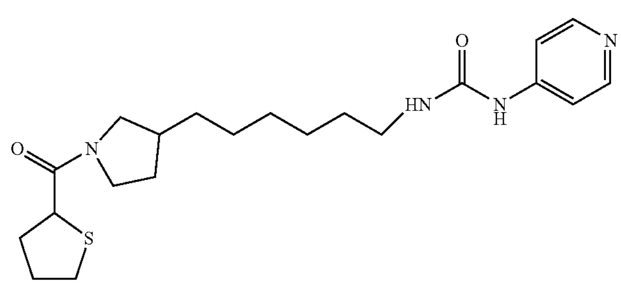 [SMILES: O=C(NCCCCCCC1CCN(C(=O)C2CCCS2)C1)Nc1ccncc1] | 405 (M + 1) |

-continued
| Preparation number | Name of Compound | Structure | MS (m/z) |
|---|---|---|---|
| BSS-TP109 | 1-(6-(1-(benzoyl)pyrrolidin-3-yl)hexyl)-2-(3-pyridinyl)urea | 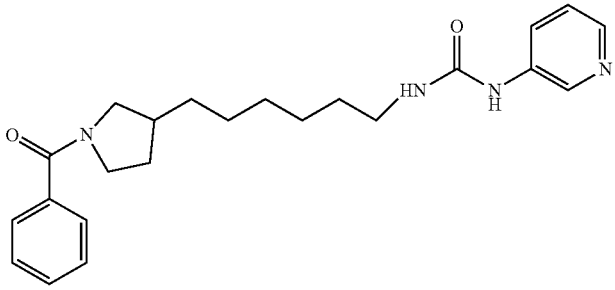 [SMILES: O=C(NCCCCCCC1CCN(C(=O)c2ccccc2)C1)Nc1cccnc1] | 395 (M + 1) |
| BSS-TP111 | 1-(6-(1-(furoyl)pyrrolidin-3-yl)hexyl)-2-(3-pyridinyl)urea | 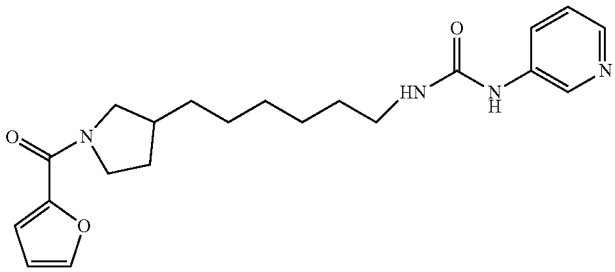 [SMILES: O=C(NCCCCCCC1CCN(C(=O)c2ccco2)C1)Nc1cccnc1] | 385 (M + 1) |
| BSS-TP110 | 1-(6-(1-(2-thienylformyl)pyrrolidin-3-yl)hexyl)-2-(3-pyridinyl)urea | 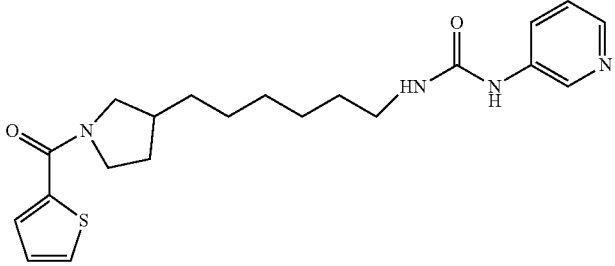 | 401 (M + 1) |
| BSS-TP112 | 1-(6-(1-(2-pyrrolylformyl)pyrrolidin-3-yl)hexyl)-2-(3-pyridinyl)urea | 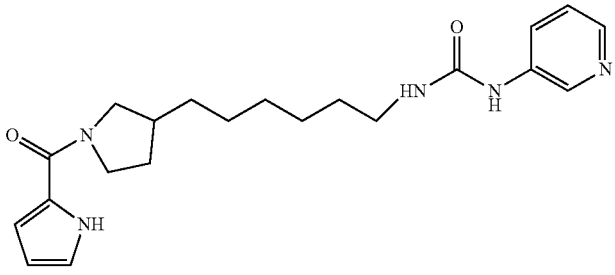 [SMILES: O=C(NCCCCCCC1CCN(C(=O)c2ccc[nH]2)C1)Nc1cccnc1] | 384 (M + 1) |
| BSS-TP113 | 1-(6-(1-(benzoyl)pyrrolidin-3-yl)hexyl)-2-(3-fluoro-4-pyridinyl)urea | 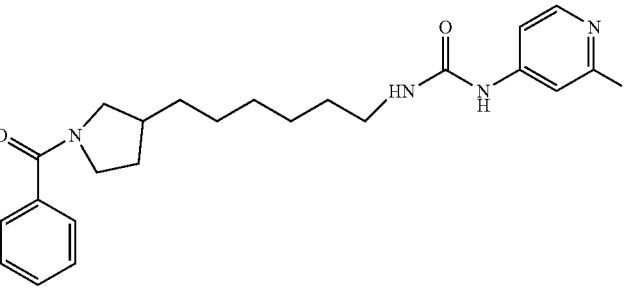 | 413 (M + 1) |

-continued

| Preparation number | Name of Compound | Structure | MS (m/z) |
|---|---|---|---|
| BSS-TP114 | 1-(6-(1-(2-pyrrolylformyl) pyrrolidin-3-yl)hexyl)-2-(3-fluoro-4-pyridinyl)urea | 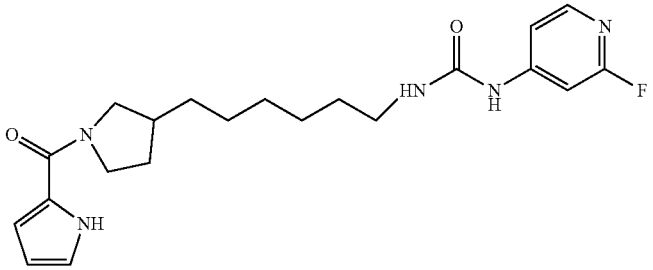 [SMILES: O=C(NCCCCCCC1CCN(C(=O)c2ccc[nH]2)C1)Nc1ccnc(F)c1] | 402 (M + 1) |
| BSS-TP115 | 1-(6-(1-(furoyl)pyrrolidin-3-yl) hexyl)-2-(3-fluoro-4-pyridinyl) urea | 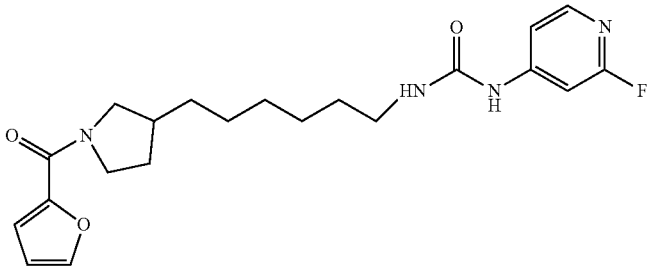 [SMILES: O=C(NCCCCCCC1CCN(C(=O)c2ccco2)C1)Nc1ccnc(F)c1] | 403 (M + 1) |
| BSS-TP116 | 1-(6-(1-(2-thienylformyl) pyrrolidin-3-yl)hexyl)-2-(3-fluoro-4-pyridinyl)urea | 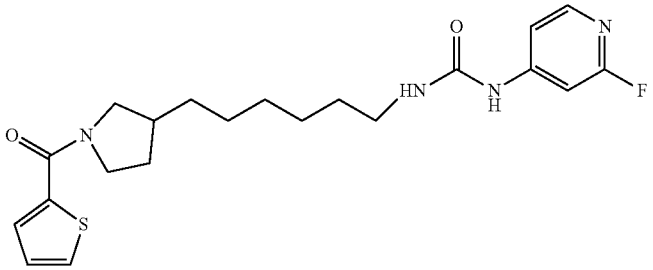 [SMILES: O=C(NCCCCCCC1CCN(C(=O)c2cccs2)C1)Nc1ccnc(F)c1] | 419 (M + 1) |
| BSS-TP117 | 1-(6-(1-(benzoyl)pyrrolidin-3-yl)hexyl)-2-(3,5-difluoro-4-pyridinyl)urea | 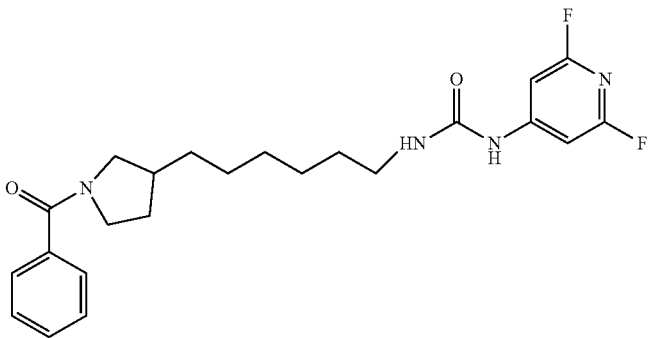 [SMILES: O=C(NCCCCCCC1CCN(C(=O)c2ccccc2)C1)Nc1cc(F)nc(F)c1] | 431 (M + 1) |
| BSS-TP118 | 1-(6-(1-(furoyl)pyrrolidin-3-yl) hexyl)-2-(3,5-difluoro-4-pyridinyl)urea | 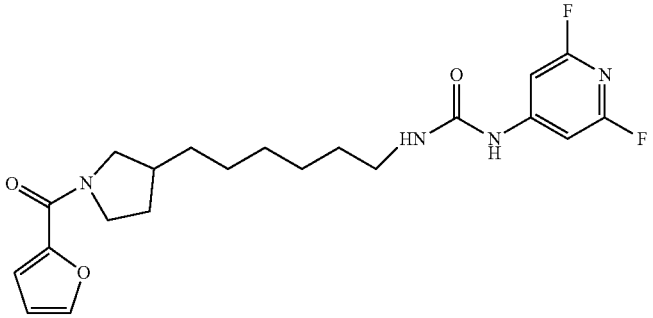 [SMILES: O=C(NCCCCCCC1CCN(C(=O)c2ccco2)C1)Nc1cc(F)nc(F)c1] | 421 (M + 1) |

| Preparation number | Name of Compound | Structure | MS (m/z) |
|---|---|---|---|
| BSS-TP119 | 1-(6-(1-(2-thienylformyl)pyrrolidin-3-yl)hexyl)-2-(3,5-difluoro-4-pyridinyl)urea | 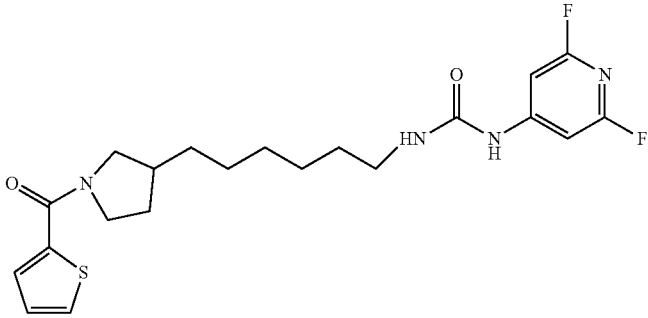 [SMILES: O=C(NCCCCCCC1CCN(C(=O)c2cccs2)C1)Nc1cc(F)nc(F)c1] | 437 (M + 1) |
| BSS-TP120 | 1-(6-(1-(2-pyrrolylformyl)pyrrolidin-3-yl)hexyl)-2-(3,5-difluoro-4-pyridinyl)urea | 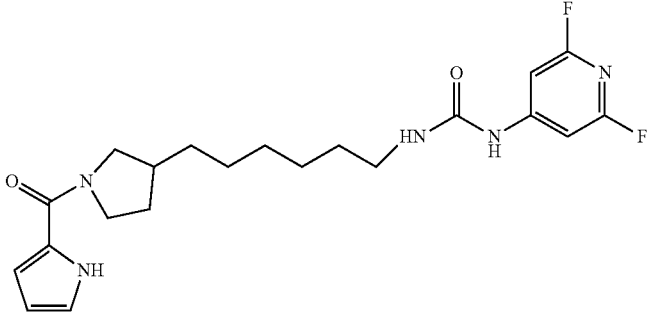 [SMILES: O=C(NCCCCCCC1CCN(C(=O)c2ccc[nH]2)C1)Nc1cc(F)nc(F)c1] | 420 (M + 1) |
| BSS-TP121 | 1-(6(1-(2-indolylformyl)pyrrolidin-3-yl)hexyl)-2-(4-pyridinyl)urea | 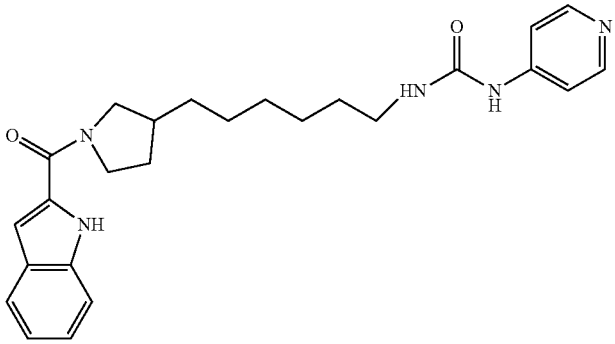 [SMILES: O=C(NCCCCCCC1CCN(C(=O)c2cc3ccccc3[nH]2)C1)Nc1ccncc1] | 434 (M + 1) |
| BSS-TP122 | 1-(6-(1-(2-benzofurylformyl)pyrrolidin-3-yl)hexyl)-2-(4-pyridinyl)urea | 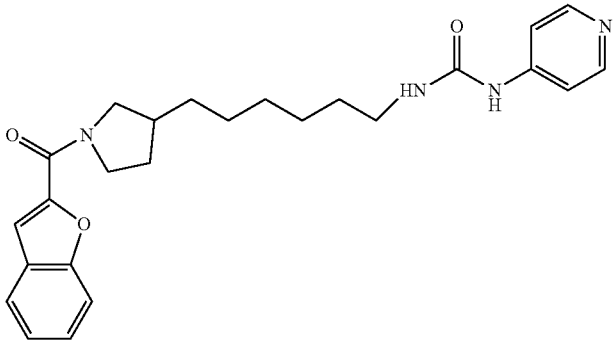 [SMILES: O=C(NCCCCCCC1CCN(C(=O)c2cc3ccccc3o2)C1)Nc1ccncc1] | 435 (M + 1) |

-continued

| Preparation number | Name of Compound | Structure | MS (m/z) |
|---|---|---|---|
| BSS-TP123 | 1-(6-(1-(2-indolylformyl)pyrrolidin-3-yl)hexyl)-2-(3-fluoro-4-pyridinyl)urea | 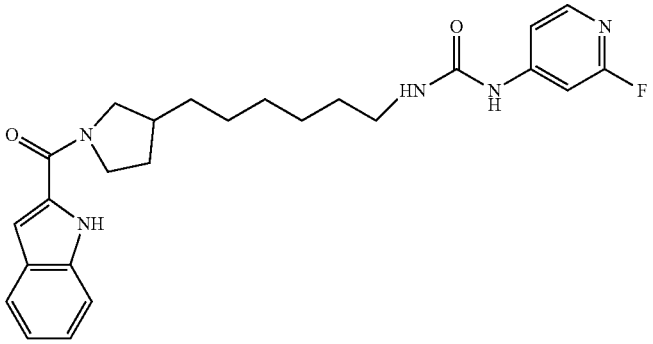 [SMILES: O=C(NCCCCCCC1CCN(C(=O)c2cc3ccccc3[nH]2)C1)Nc1ccnc(F)c1] | 452 (M + 1) |
| BSS-TP124 | 1-(6-(1-(2-benzofurylformyl)pyrrolidin-3-yl)hexyl)-2-(3-fluoro-4-pyridinyl)urea | 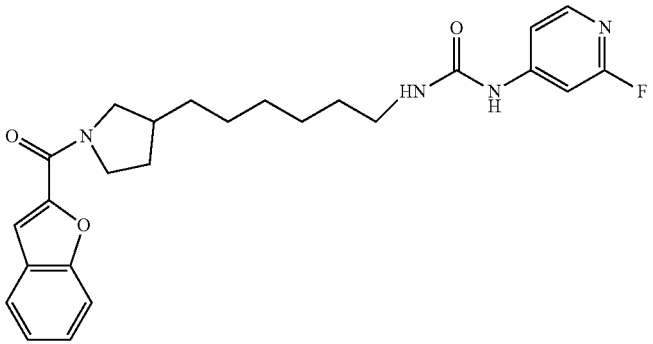 [SMILES: O=C(NCCCCCCC1CCN(C(=O)c2cc3ccccc3o2)C1)Nc1ccnc(F)c1] | 453 (M + 1) |
| BSS-TP125 | 1-(6-(1-(2,6-dimethoxybenzoyl)pyrrolidin-3-yl)hexyl)-2-(3,5-difluoro-4-pyridinyl)urea | 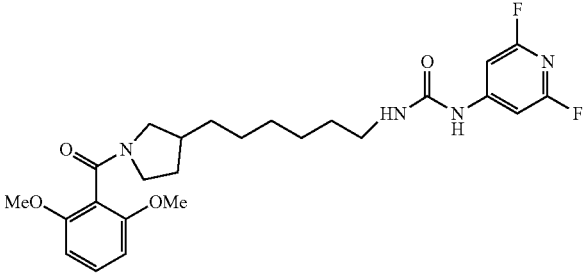 [SMILES: COc1cccc(OC)c1C(=O)N1CCC(CCCCCCNC(=O)Nc2cc(F)nc(F)c2)C1] | 491 (M + 1) |
| BSS-TP126 | 1-(7-(1-(2,6-dimethoxybenzoyl)pyrrolidin-3-yl)heptyl)-2-(4-pyridinyl)urea | 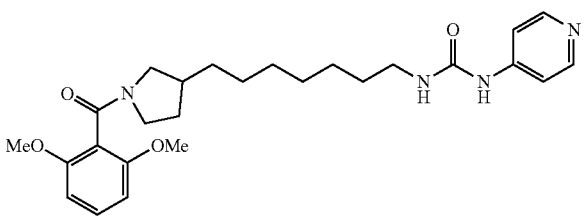 [SMILES: COc1cccc(OC)c1C(=O)N1CCC(CCCCCCCNC(=O)Nc2ccncc2)C1] | 469 (M + 1) |
| BSS-TP127 | 1-(4-(1-(2,6-dimethoxybenzoyl)pyrrolidin-3-yl)butyl)-2-(4-pyridinyl)urea | 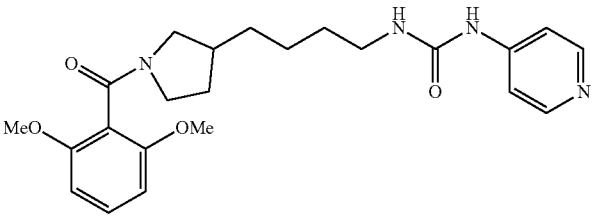 [SMILES: COc1cccc(OC)c1C(=O)N1CCC(CCCCNC(=O)Nc2ccncc2)C1] | 427 (M + 1) |

-continued

| Preparation number | Name of Compound | Structure | MS (m/z) |
|---|---|---|---|
| BSS-TP128 | 1-(7-(1-(furoyl)pyrrolidin-3-yl)heptyl)-2-(4-pyridinyl)urea | 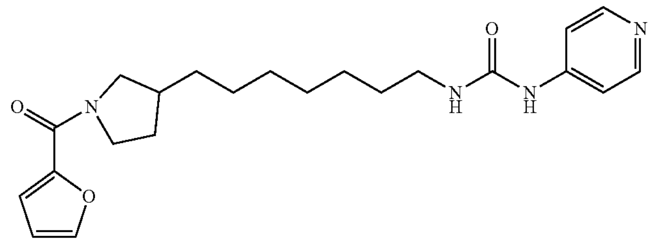 [SMILES: O=C(NCCCCCCCC1CCN(C(=O)c2ccco2)C1)Nc1ccncc1] | 399 (M + 1) |
| BSS-TP129 | 1-(7-(1-(2-pyrrolylformyl)pyrrolidin-3-yl)heptyl)-2-(4-pyridinyl)urea | 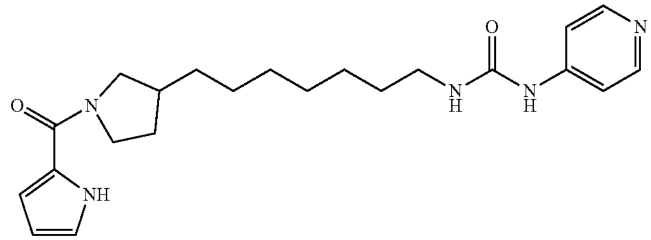 [SMILES: O=C(NCCCCCCCC1CCN(C(=O)c2ccc[nH]2)C1)Nc1ccncc1] | 398 (M + 1) |
| BSS-TP130 | 1-(7-(1-(2,6-dimethoxybenzoyl)pyrrolidin-3-yl)heptyl)-2-(3-fluoro-4-pyridinyl)urea | 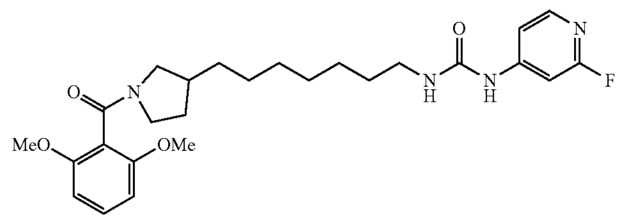 [SMILES: COc1cccc(OC)c1C(=O)N1CCC(CCCCCCCNC(=O)Nc2ccnc(F)c2)C1] | 487 (M + 1) |
| BSS-TP131 | 1-(7-(1-benzoyl)pyrrolidin-3-yl)heptyl)-2-(4-pyridinyl)urea | 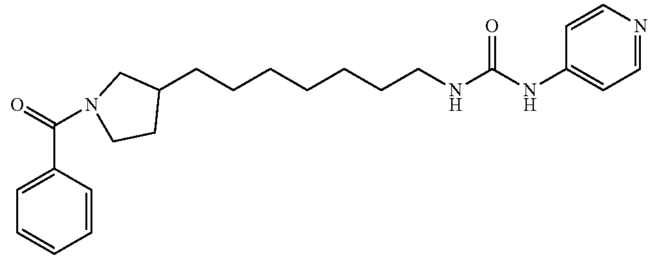 [SMILES: O=C(NCCCCCCCC1CCN(C(=O)c2ccccc2)C1)Nc1ccncc1] | 409 (M + 1) |
| BSS-TP132 | 1-(7-(1-benzoyl)pyrrolidin-3-yl)heptyl)-2-(3-fluoro-4-pyridinyl)urea | 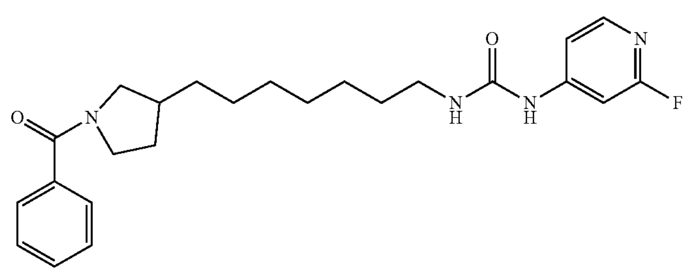 [SMILES: O=C(NCCCCCCCC1CCN(C(=O)c2ccccc2)C1)Nc1ccnc(F)c1] | 427 (M + 1) |

Example 14

The effect of samples on the proliferation of human tumor cells in vitro was determined by CCK-8 cell proliferation assay.

TABLE 1

Cell lines and culture conditions

| Cell line | Complete growth medium | | Temperature | Atmosphere | |
|---|---|---|---|---|---|
| | base medium | serum | | air | $CO_2$ |
| Human lung adenocarcinoma cell A549 | RPMI-1640 | FBS | 37° C. | 95% | 5% |
| Human hepatoma cell HepG2 | MEM | FBS | 37° C. | 95% | 5% |
| Human esophageal cancer cell TE-1 | DMEM | FBS | 37° C. | 95% | 5% |
| Human gastric cancer cell MKN45 | RPMI-1640 | FBS | 37° C. | 95% | 5% |
| Human colon cancer cell HCT-116 | McCoy's 5A | FBS | 37° C. | 95% | 5% |
| Human multiple myeloma cell RPMI 8226 | RPMI-1640 | FBS | 37° C. | 95% | 5% |
| Human pancreatic cancer cell CFPAC-1 | DMEM | FBS | 37° C. | 95% | 5% |
| Human pancreatic cancer cell PANC-1 | DMEM | FBS | 37° C. | 95% | 5% |

The cells were assayed through a method including the following steps:

1) The cells were digested, counted, and prepared into a cell suspension in a corresponding culture medium (Table 1) ($5 \times 10^4$ cells/ml for CFPAC-1 and RPMI 8226, and $3.5 \times 10^4$ cells/ml for rest cells). The cell suspension was added to each well of a 96-well plate in 100 µl well.

2) Then the 96-well plate was incubated for 24 hrs in an incubator at 37° C. and 5% $CO_2$.

3) The drug was diluted with the culture medium to the required working concentration. 100 µl of the corresponding drug containing medium was added to each well. A negative control group (added with drug-free culture medium) was also set.

4) Then the 96-well plate was incubated for 24 hrs in an incubator at 37° C. and 5% $CO_2$.

5) The 96-well plate was stained with CCK-8, and The OD value was determined at λ=450 nm.

a) 10 µl of CCK-8 was added to each well, and incubated in the incubator for another 2-3 hrs.

b) The content was mixed uniformly by shaking gently on a shaker for 10 min, and the bubbles in the 96-well plate were removed.

c) The OD value of each well was read on a plate reader at λ=450 nm, and the inhibition rate was calculated.

6) The inhibition rate in each group was calculated.

$$\text{Inhibition (\%)} = \frac{OD \text{ value of negative control group} - OD \text{ value of experimental group}}{OD \text{ value of negative control group}} \times 100\%$$

The data of cell assay are shown in the following table: ($IC_{50}$: unit µM):

| Drug number | A549 | HepG2 | TE-1 | MKN-45 | HCT116 | RPMI8226 | CFPAC-1 |
|---|---|---|---|---|---|---|---|
| FK866 | 0.037 | 0.099 | 0.112 | 0.039 | 0.092 | 0.02 | 0.037 |
| BSS-TP007 | 0.031 | 0.069 | 0.076 | 0.057 | 0.033 | 0.017 | 0.028 |
| BSS-TP008 | 0.055 | 0.051 | 0.058 | 0.043 | 0.077 | 0.033 | 0.022 |
| BSS-TP009 | 0.029 | 0.046 | 0.049 | 0.063 | 0.021 | 0.026 | 0.039 |
| BSS-TP010 | 0.036 | 0.041 | 0.042 | 0.034 | 0.025 | 0.02 | 0.038 |
| BSS-TP011 | 0.033 | 0.077 | 0.081 | 0.036 | 0.071 | 0.032 | 0.029 |
| BSS-TP012 | 0.067 | 0.124 | 0.137 | 0.059 | 0.051 | 0.03 | 0.038 |
| BSS-TP013 | 0.081 | 0.133 | 0.098 | 0.073 | 0.068 | 0.045 | 0.041 |
| BSS-TP014 | 0.117 | 0.089 | 0.082 | 0.091 | 0.062 | 0.05 | 0.051 |
| BSS-TP015 | 0.031 | 0.039 | 0.057 | 0.033 | 0.043 | 0.022 | 0.028 |
| BSS-TP016 | 0.03 | 0.059 | 0.055 | 0.046 | 0.041 | 0.03 | 0.032 |
| BSS-TP017 | 0.041 | 0.077 | 0.069 | 0.055 | 0.057 | 0.042 | 0.041 |
| BSS-TP018 | 0.038 | 0.061 | 0.088 | 0.039 | 0.051 | 0.038 | 0.033 |
| BSS-TP019 | 0.072 | 0.085 | 0.132 | 0.071 | 0.039 | 0.044 | 0.049 |
| BSS-TP020 | 0.093 | 0.049 | 0.091 | 0.052 | 0.047 | 0.033 | 0.034 |
| BSS-TP021 | 0.033 | 0.042 | 0.065 | 0.065 | 0.077 | 0.042 | 0.031 |
| BSS-TP022 | 0.037 | 0.053 | 0.046 | 0.033 | 0.061 | 0.038 | 0.037 |
| BSS-TP023 | 0.053 | 0.072 | 0.102 | 0.076 | 0.069 | 0.042 | 0.046 |
| BSS-TP024 | 0.059 | 0.074 | 0.111 | 0.081 | 0.073 | 0.049 | 0.039 |
| BSS-TP025 | 0.062 | 0.077 | 0.065 | 0.053 | 0.054 | 0.04 | 0.037 |
| BSS-TP026 | 0.069 | 0.083 | 0.072 | 0.071 | 0.092 | 0.051 | 0.042 |
| BSS-TP027 | 0.088 | 0.102 | 0.093 | 0.065 | 0.092 | 0.055 | 0.059 |
| BSS-TP028 | 0.041 | 0.059 | 0.057 | 0.044 | 0.063 | 0.042 | 0.031 |
| BSS-TP029 | 0.031 | 0.047 | 0.042 | 0.047 | 0.076 | 0.033 | 0.038 |

| Drug number | A549 | HepG2 | TE-1 | MKN-45 | HCT116 | RPMI8226 | CFPAC-1 |
|---|---|---|---|---|---|---|---|
| BSS-TP030 | 0.042 | 0.063 | 0.06 | 0.057 | 0.062 | 0.046 | 0.04 |
| BSS-TP031 | 0.059 | 0.051 | 0.068 | 0.045 | 0.053 | 0.039 | 0.033 |
| BSS-TP032 | 0.073 | 0.099 | 0.117 | 0.074 | 0.069 | 0.058 | 0.039 |
| BSS-TP033 | 0.064 | 0.082 | 0.087 | 0.065 | 0.072 | 0.053 | 0.056 |
| BSS-TP034 | 0.044 | 0.076 | 0.094 | 0.055 | 0.068 | 0.036 | 0.043 |
| BSS-TP035 | 0.039 | 0.081 | 0.073 | 0.047 | 0.066 | 0.029 | 0.035 |
| BSS-TP036 | 0.058 | 0.126 | 0.094 | 0.053 | 0.078 | 0.049 | 0.042 |
| BSS-TP037 | 0.038 | 0.061 | 0.064 | 0.053 | 0.029 | 0.026 | 0.035 |
| BSS-TP038 | 0.031 | 0.067 | 0.082 | 0.047 | 0.038 | 0.022 | 0.029 |
| BSS-TP039 | 0.046 | 0.06 | 0.073 | 0.047 | 0.071 | 0.038 | 0.025 |
| BSS-TP040 | 0.043 | 0.049 | 0.065 | 0.031 | 0.052 | 0.024 | 0.029 |
| BSS-TP101 | 0.035 | 0.05 | 0.064 | 0.039 | 0.022 | 0.021 | 0.029 |
| BSS-TP102 | 0.023 | 0.035 | 0.029 | 0.03 | 0.027 | 0.01 | 0.013 |
| BSS-TP103 | 0.028 | 0.043 | 0.05 | 0.036 | 0.088 | 0.015 | 0.031 |
| BSS-TP104 | 0.033 | 0.075 | 0.062 | 0.046 | 0.057 | 0.029 | 0.033 |
| BSS-TP105 | 0.043 | 0.061 | 0.076 | 0.032 | 0.053 | 0.02 | 0.037 |
| BSS-TP106 | 0.068 | 0.119 | 0.097 | 0.058 | 0.066 | 0.047 | 0.046 |
| BSS-TP107 | 0.055 | 0.137 | 0.082 | 0.053 | 0.076 | 0.051 | 0.058 |
| BSS-TP108 | 0.049 | 0.092 | 0.073 | 0.049 | 0.059 | 0.032 | 0.041 |
| BSS-TP109 | 0.029 | 0.071 | 0.088 | 0.053 | 0.047 | 0.023 | 0.026 |
| BSS-TP110 | 0.044 | 0.116 | 0.109 | 0.075 | 0.073 | 0.056 | 0.052 |
| BSS-TP111 | 0.061 | 0.087 | 0.133 | 0.077 | 0.062 | 0.053 | 0.042 |
| BSS-TP112 | 0.052 | 0.081 | 0.093 | 0.059 | 0.078 | 0.042 | 0.036 |
| BSS-TP113 | 0.033 | 0.083 | 0.077 | 0.042 | 0.041 | 0.038 | 0.038 |
| BSS-TP114 | 0.049 | 0.072 | 0.076 | 0.051 | 0.085 | 0.039 | 0.033 |
| BSS-TP115 | 0.051 | 0.079 | 0.088 | 0.04 | 0.068 | 0.046 | 0.039 |
| BSS-TP116 | 0.039 | 0.081 | 0.069 | 0.079 | 0.083 | 0.031 | 0.047 |
| BSS-TP117 | 0.058 | 0.049 | 0.047 | 0.045 | 0.053 | 0.036 | 0.037 |
| BSS-TP118 | 0.059 | 0.064 | 0.081 | 0.062 | 0.061 | 0.024 | 0.042 |
| BSS-TP119 | 0.072 | 0.083 | 0.087 | 0.061 | 0.05 | 0.043 | 0.038 |
| BSS-TP120 | 0.047 | 0.053 | 0.049 | 0.042 | 0.066 | 0.028 | 0.035 |
| BSS-TP121 | 0.069 | 0.072 | 0.074 | 0.032 | 0.083 | 0.052 | 0.051 |
| BSS-TP122 | 0.067 | 0.071 | 0.063 | 0.061 | 0.069 | 0.026 | 0.049 |
| BSS-TP123 | 0.063 | 0.059 | 0.065 | 0.069 | 0.058 | 0.032 | 0.059 |
| BSS-TP124 | 0.056 | 0.063 | 0.082 | 0.064 | 0.073 | 0.039 | 0.042 |
| BSS-TP125 | 0.046 | 0.052 | 0.043 | 0.057 | 0.049 | 0.028 | 0.047 |
| BSS-TP126 | 0.055 | 0.092 | 0.088 | 0.032 | 0.063 | 0.033 | 0.053 |
| BSS-TP127 | 0.075 | 0.102 | 0.135 | 0.109 | 0.076 | 0.034 | 0.058 |
| BSS-TP128 | 0.068 | 0.110 | 0.124 | 0.051 | 0.097 | 0.036 | 0.053 |
| BSS-TP129 | 0.073 | 0.093 | 0.096 | 0.049 | 0.072 | 0.023 | 0.028 |
| BSS-TP130 | 0.056 | 0.055 | 0.061 | 0.073 | 0.046 | 0.038 | 0.043 |
| BSS-TP131 | 0.043 | 0.067 | 0.069 | 0.047 | 0.075 | 0.029 | 0.036 |
| BSS-TP132 | 0.051 | 0.061 | 0.077 | 0.039 | 0.065 | 0.034 | 0.03 |

What is claimed is:

1. A pyrrolidine derivative or a pharmaceutically acceptable salt thereof, wherein the pyrrolidine derivative has a structure selected from the group consisting of:

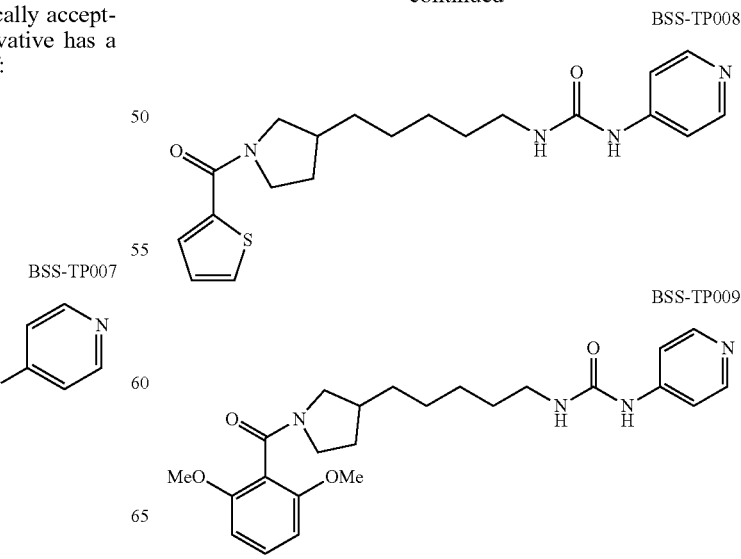

BSS-TP010
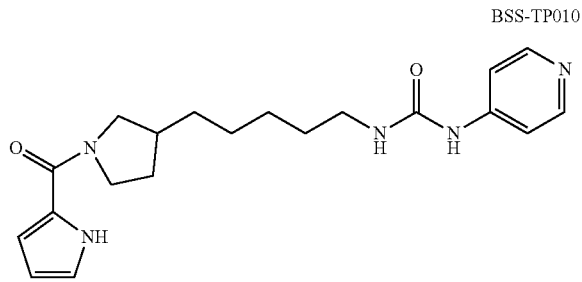
BSS-TP011
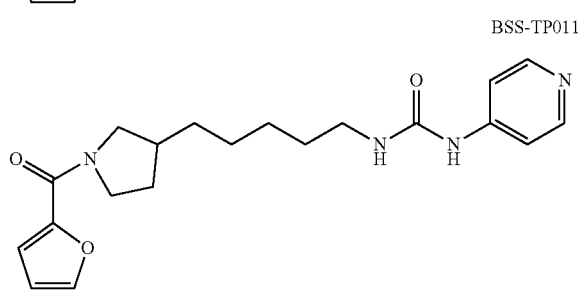
BSS-TP012
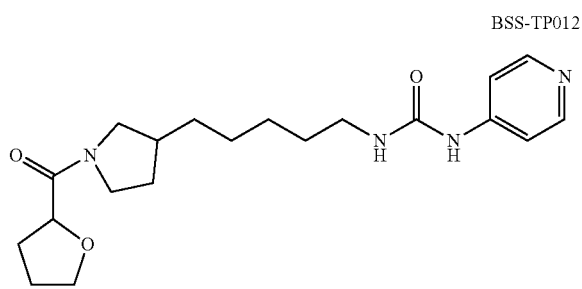
BSS-TP013
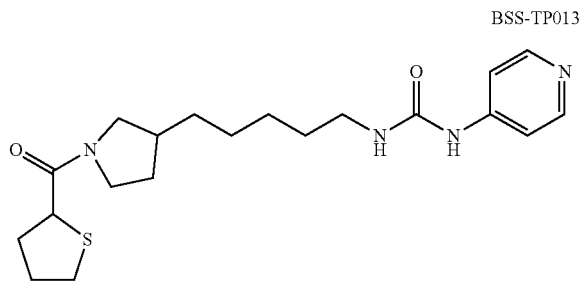
BSS-TP014
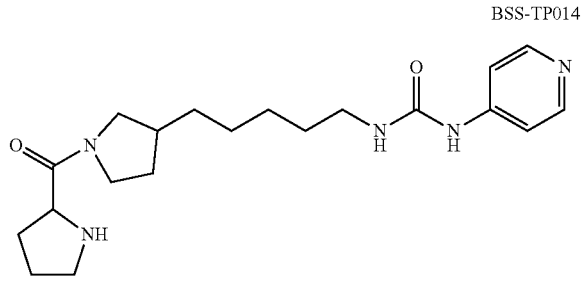
BSS-TP015
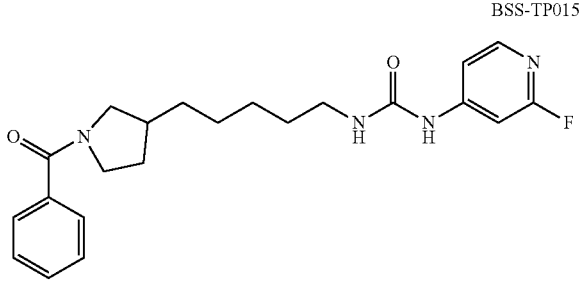
BSS-TP016
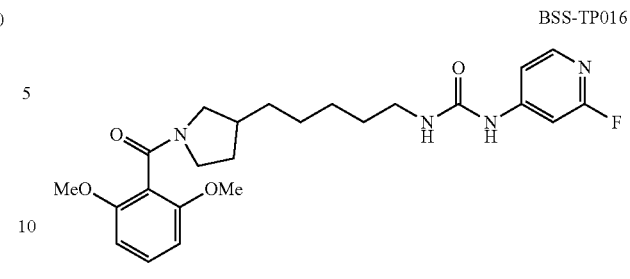
BSS-TP017
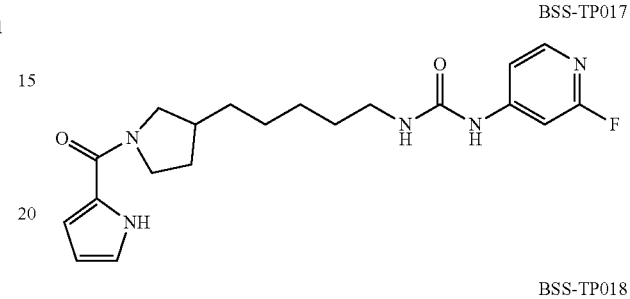
BSS-TP018
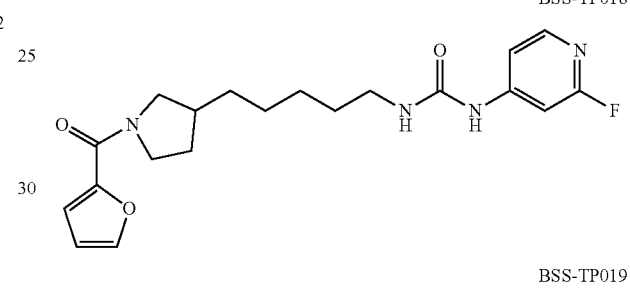
BSS-TP019
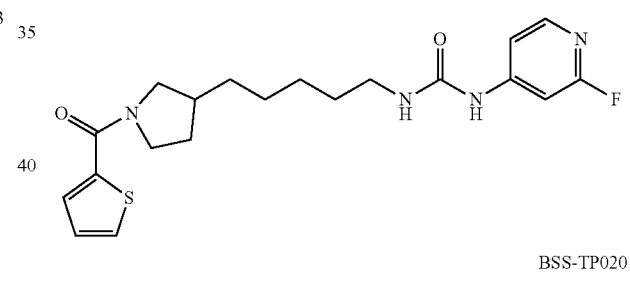
BSS-TP020
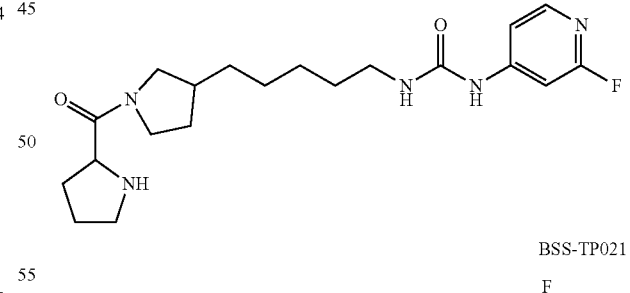
BSS-TP021
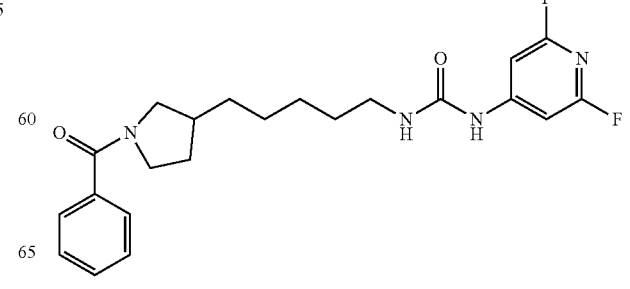

BSS-TP022
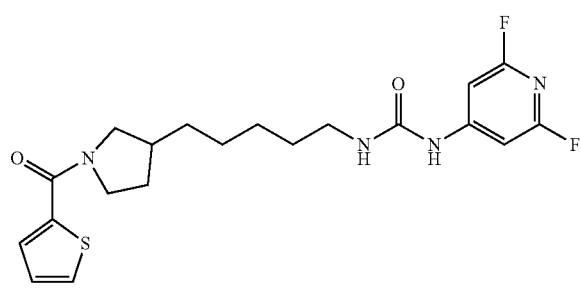
BSS-TP027
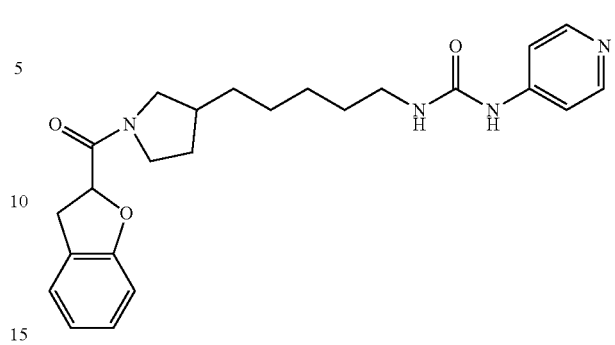
BSS-TP023
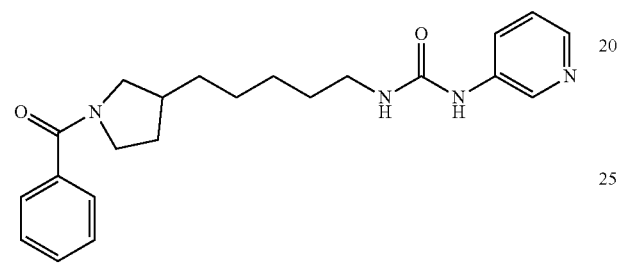
BSS-TP028
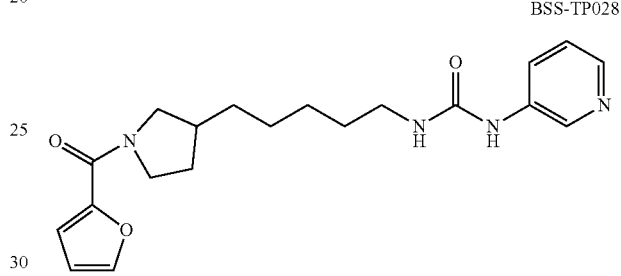
BSS-TP024
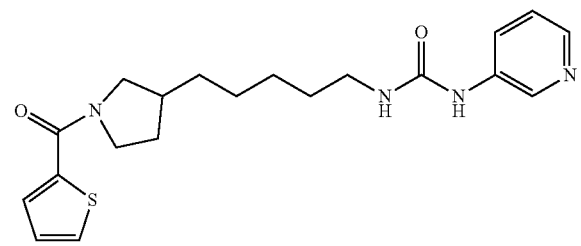
BSS-TP029
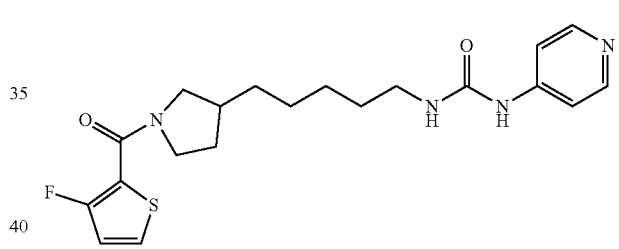
BSS-TP025
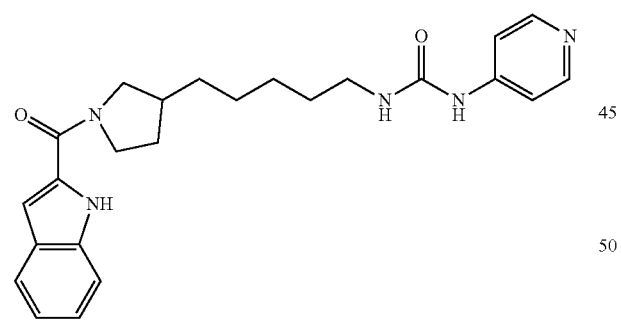
BSS-TP030
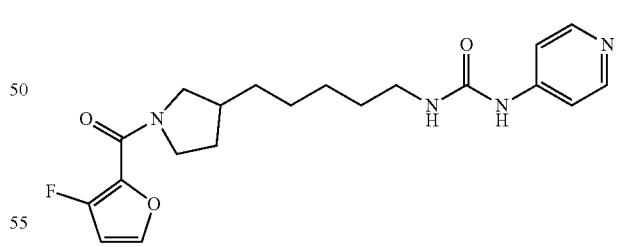
BSS-TP026
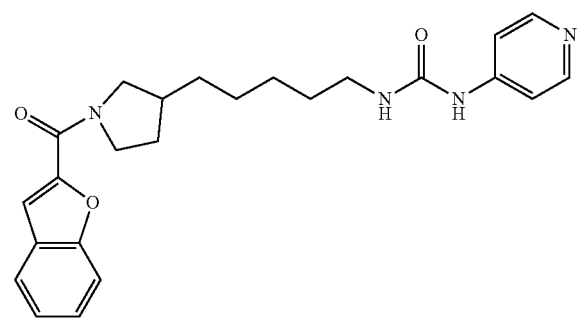
BSS-TP031
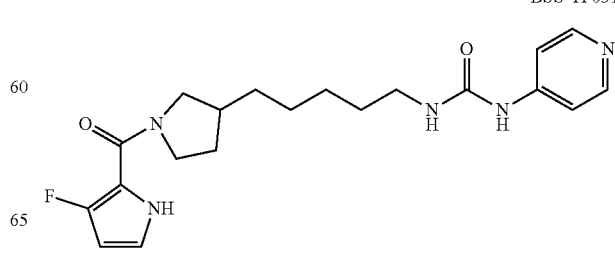

BSS-TP032
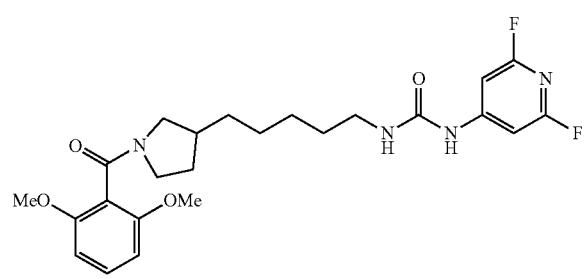
BSS-TP037
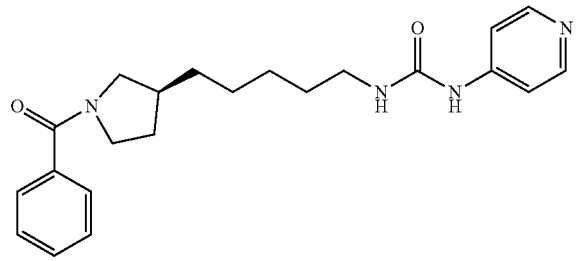
BSS-TP033
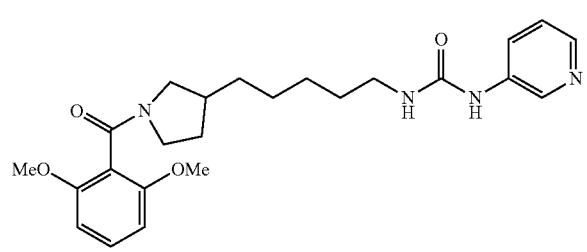
BSS-TP038
BSS-TP034
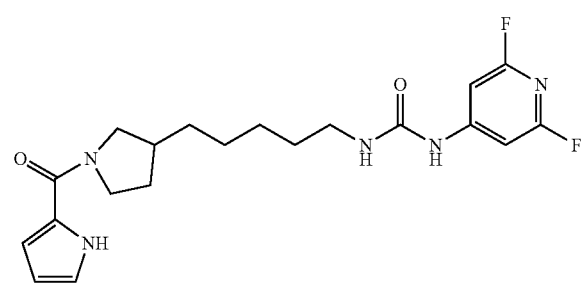
BSS-TP039
BSS-TP035
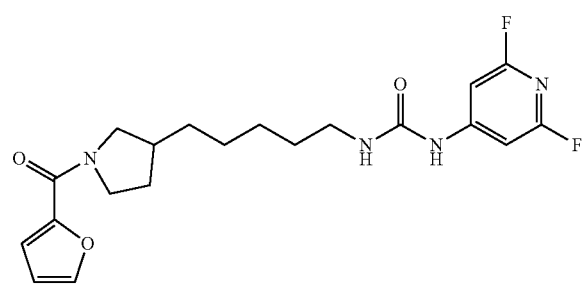
BSS-TP040
BSS-TP036
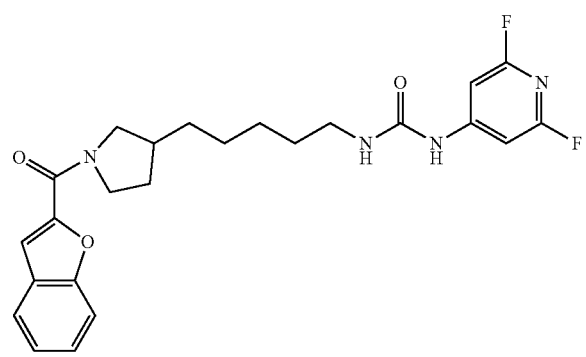
BSS-TP101
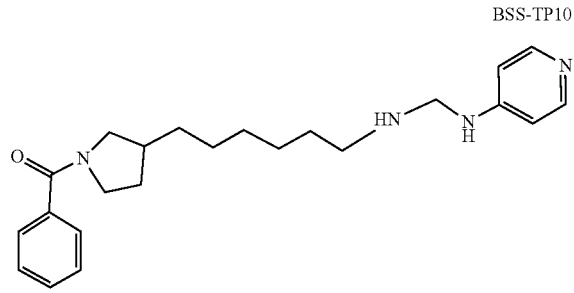

73
-continued
BSS-TP102
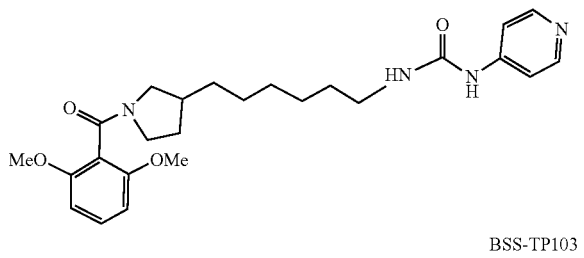
BSS-TP103
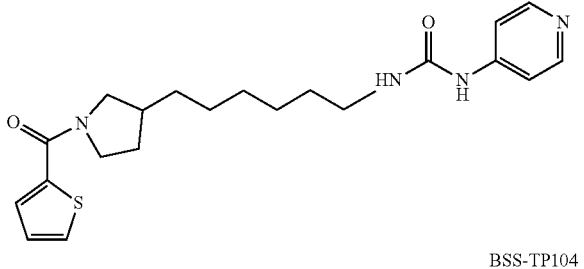
BSS-TP104
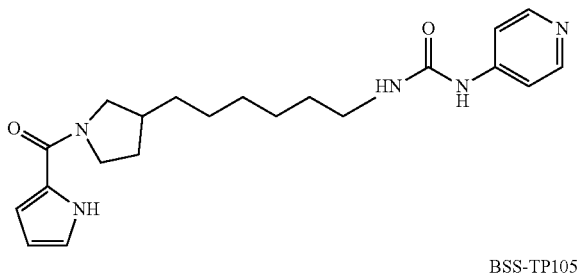
BSS-TP105
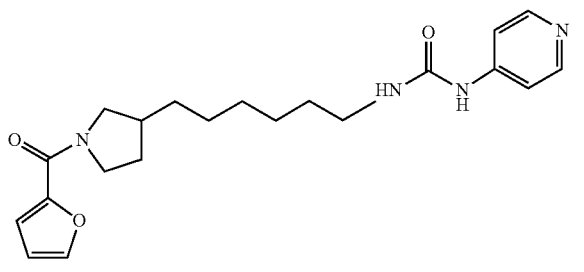
BSS-TP106
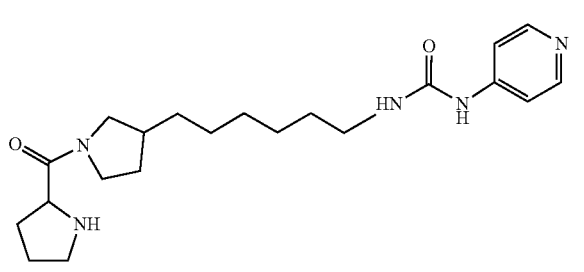
BSS-TP107
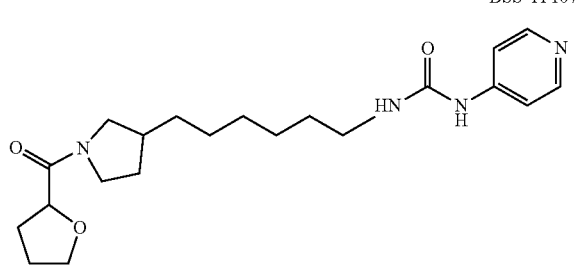
74
-continued
BSS-TS108
BSS-TP109
BSS-TP110
BSS-TP111
BSS-TP112
BSS-TP113

BSS-TP114
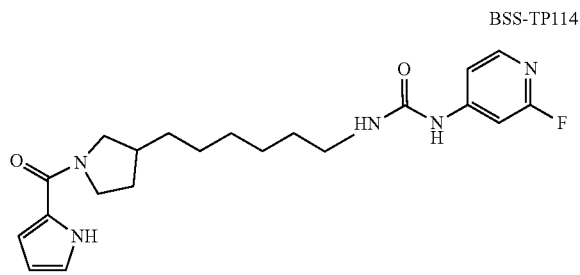
BSS-TP115
BSS-TP116
BSS-TP117
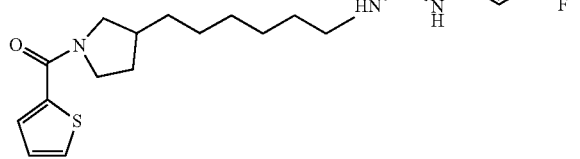
BSS-TP118
BSS-TP119
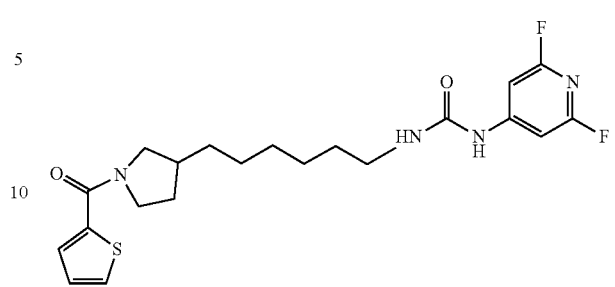
BSS-TP120
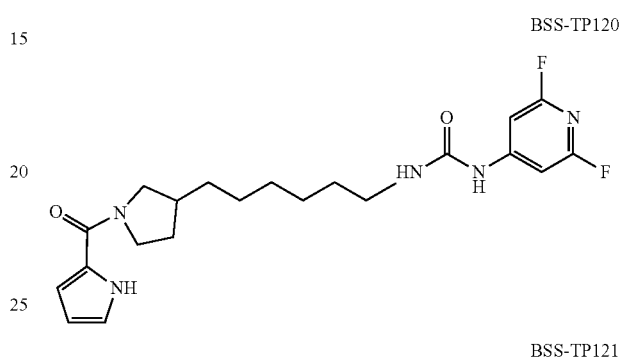
BSS-TP121
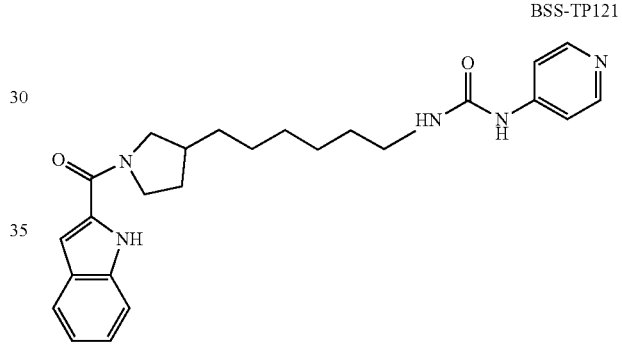
BSS-TP122
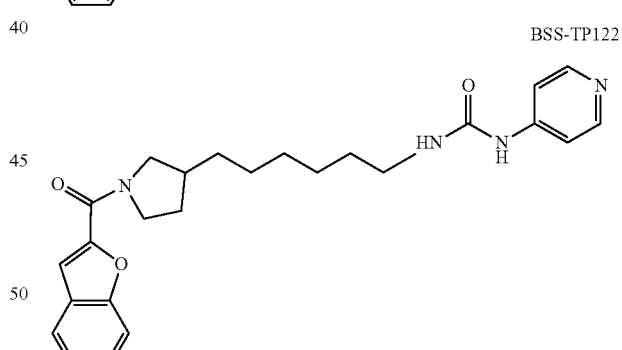
BSS-TP123
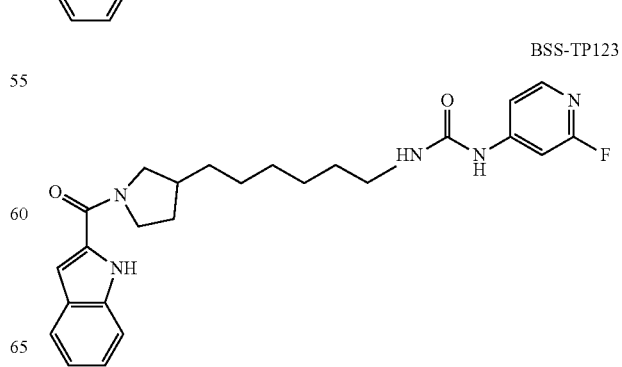

-continued
BSS-TP124
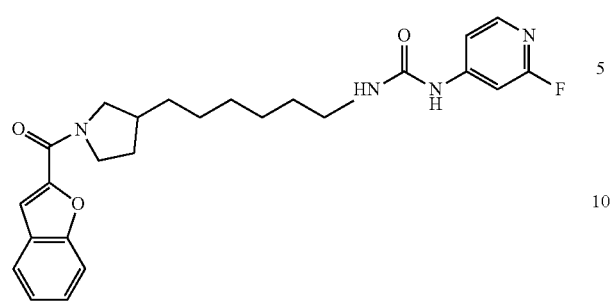
BSS-TP125
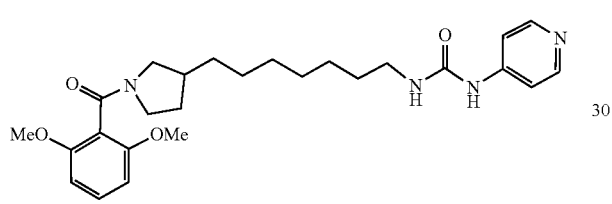
BSS-TP126
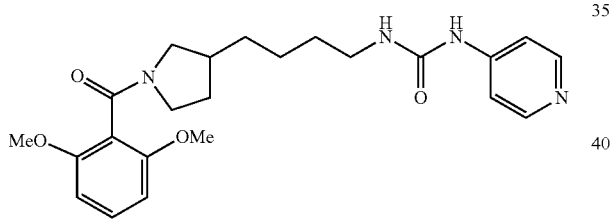
BSS-TP127
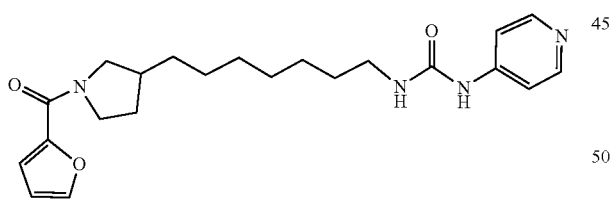
BSS-TP128
-continued
BSS-TP129
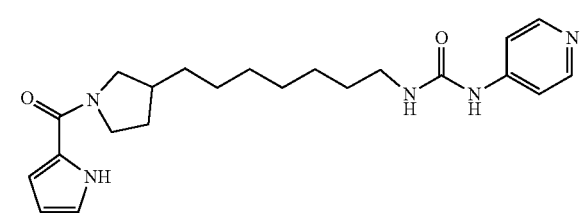
BSS-TP130
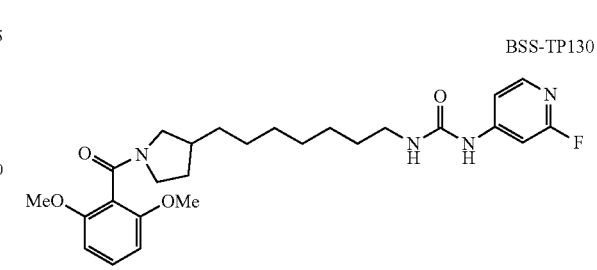
BSS-TP131
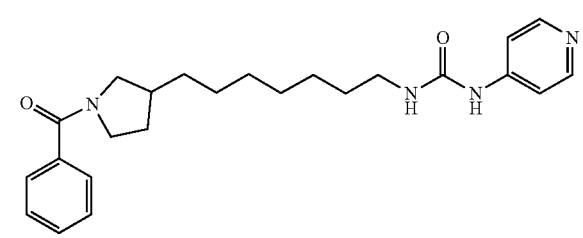
BSS-TP132
* * * * *